(12) United States Patent
Scurtescu

(10) Patent No.: US 10,595,960 B2
(45) Date of Patent: *Mar. 24, 2020

(54) ULTRASONIC METHODS AND DEVICES FOR DENTAL TREATMENT

(71) Applicant: SmileSonica Inc., Edmonton (CA)

(72) Inventor: Cristian Scurtescu, Edmonton (CA)

(73) Assignee: SMILESONICA INC., Edmonton (CA)

( * ) Notice: Subject to any disclaimer, the term of this patent is extended or adjusted under 35 U.S.C. 154(b) by 344 days.

This patent is subject to a terminal disclaimer.

(21) Appl. No.: 14/991,081

(22) Filed: Jan. 8, 2016

(65) Prior Publication Data

US 2016/0120615 A1    May 5, 2016

Related U.S. Application Data

(63) Continuation of application No. 13/642,392, filed as application No. PCT/CA2011/000498 on Apr. 29, 2011, now Pat. No. 9,232,986.

(Continued)

(51) Int. Cl.
*A61C 1/07* (2006.01)
*A61C 7/00* (2006.01)

(Continued)

(52) U.S. Cl.
CPC ............. *A61C 1/07* (2013.01); *A61C 1/0007* (2013.01); *A61C 7/00* (2013.01); *A61C 19/06* (2013.01);

(Continued)

(58) Field of Classification Search
CPC ....... A61C 17/20; A61C 17/3481; A61C 1/07; A61C 1/00; A61N 7/00; A61M 37/0092
See application file for complete search history.

(56) References Cited

U.S. PATENT DOCUMENTS 3,380,446 A * 4/1968 Martin .................... A61B 5/103
134/184
4,127,125 A * 11/1978 Takemoto .............. A61C 17/20
433/119

(Continued)

FOREIGN PATENT DOCUMENTS

CA           2650778 A1    11/2007
WO         95/04506 A1     2/1995
WO         99/58080 A1    11/1999

*Primary Examiner* — Yogesh P Patel
(74) *Attorney, Agent, or Firm* — Snell & Wilmer L.L.P.

(57) ABSTRACT

Devices and methods for ultrasonic dental treatment are described, wherein the devices and methods can comprise a flexible array of cooperative ultrasound transducers. The array can contain individual ultrasonic transducers that can perform both functions of emitting and sensing. The transducers can have the ability to interchange their functions from emitting to sensing. The transducers can cooperate in providing an ultrasound treatment and each transducer can be independently controlled by an external source controller. An ultrasound system is provided comprising: an ultrasound transducer sensor array operable to emit or sense ultrasound, wherein the timing and intensity of emission may be controlled by an electronic controller based on a feedback signal from the sensors. In addition the ultrasound system can also have the ability to sense coupling to a treatment tissue. This ability to sense proper coupling can improve the efficacy of the treatment.

9 Claims, 14 Drawing Sheets

Related U.S. Application Data

(60) Provisional application No. 61/330,235, filed on Apr. 30, 2010.

(51) Int. Cl.
    *A61N 7/00*      (2006.01)
    *A61C 1/00*      (2006.01)
    *A61C 19/06*    (2006.01)
    *A61B 17/00*     (2006.01)
    *A61B 18/00*     (2006.01)

(52) U.S. Cl.
    CPC ...... *A61N 7/00* (2013.01); *A61B 2017/00106* (2013.01); *A61B 2018/00648* (2013.01); *A61N 2007/0026* (2013.01); *A61N 2007/0078* (2013.01)

(56) References Cited

U.S. PATENT DOCUMENTS

| | | |
|---|---|---|
| 5,496,256 A | 3/1996 | Bock et al. |
| 6,050,821 A | 4/2000 | Klaassen et al. |
| 8,079,966 B2 | 12/2011 | El-Bialy et al. |
| 2005/0196725 A1 | 9/2005 | Fu |
| 2007/0157404 A1* | 7/2007 | Brewer .............. A46B 15/0002 15/22.1 |
| 2010/0068670 A1 | 3/2010 | Yamamoto et al. |
| 2011/0256503 A1* | 10/2011 | Fraser .................... A61C 17/20 433/119 |

\* cited by examiner

ULTRASONIC METHODS AND DEVICES FOR DENTAL TREATMENT

PRIORITY

This application is a continuation of U.S. patent application Ser. No. 13/642,392, entitled "ULTRASONIC METHOD AND DEVICES FOR DENTAL TREATMENT", filed Oct. 19, 2012, which is a 371 application of PCT/CA2011/000498 filed Apr. 29, 2011, which claims priority to U.S. Provisional Patent Application No. 61/330,235 filed Apr. 30, 2010, all of which are incorporated herein by reference in their entireties.

TECHNICAL FIELD

This disclosure relates to ultrasound stimulation and more specifically, to methods and devices for applying ultrasound stimulation in dental treatment.

BACKGROUND

It is generally known that both healthy support of teeth (i.e. a high tooth-root length to tooth-crown height ratio), and an increased capacity to withstand occlusal forces (i.e. a high volume of alveolar bone capable of supporting a tooth root) are important factors in dental wellbeing. Unfortunately, dental trauma or orthodontic treatment (for example, wearing orthodontic braces) may cause shortening or "resorption" of tooth root and/or alveolar bone, thereby resulting in a major cause of tooth mobility and/or loss. For instance, in cases of tooth root resorption, where the tooth-root to tooth-crown ratio may be adversely affected, increased tooth mobility can be observed and splinting of the impacted "loose" teeth may be required. In addition, severe cases of root resorption may lead to tooth loss. In severe cases of alveolar bone resorption, where the volume and height of alveolar bone supporting the tooth root is greatly reduced, complete tooth loss may arise and the insertion of a dental implant may be required. Unfortunately, the body's efficacy of repairing tooth root resorption can depend upon the degree and extent (surface area) of damaged root, and can result in ankylosis where the bone attaches directly to the root surface. Further, implants for lost teeth prove difficult, particularly in circumstances where the implant must be inserted into the severely resorbed alveolar bone.

Several non-invasive therapeutic methods for healing dental tissue are known, such as, for example, techniques using electrical stimulation, pulsed electromagnetic field, or low intensity pulsed ultrasound. For instance, ultrasound devices have been used in an attempt to treat orthodontically-induced tooth root resorption in humans, to stimulate dental tissue formation and to enhance teeth eruption. It is known that the efficacy of ultrasound treatments may depend upon the pulse duration and intensity applied. Indeed, where suitable levels of ultrasound are applied, it is known that ultrasound pulses can be effective for enhancing dental tissue healing, and for treating declining tooth-root to tooth-crown ratio (known as the "tooth to root ratio problem").

Current ultrasound devices, however, can be bulky or cumbersome, requiring that a dentist positions the device on a patient's tooth or an orthodontic bracket. Alternatively, some devices may need to be custom-made according to the specific dimensions of the patient's tooth crown in order to ensure positioning of the device on an individual tooth.

In addition to the foregoing application difficulties, typical ultrasound devices do not provide more than one ultrasound emitter (transducer), and thus may only emit ultrasound to a single tooth at a time, and from one direction. Attempts have been made to utilize ultrasound "trays", which are capable of propagating ultrasound over a larger treatment area, however, such trays are often manufactured from a stiff material which can be uncomfortable for patients.

Current ultrasound devices, such as the "trays", typically lack accurate control means for maintaining or adjusting the intensity of ultrasound being emitted, making it difficult to control the level of ultrasound that is applied to a treatment area. This lack of control further prevents the ability to monitor and regulate the amount of ultrasound applied to an individual tooth, and to selectively treat individual teeth or groups of teeth as desired. In addition to a lack of control, current devices also lack accurate feedback means for sensing or measuring the ultrasound received at the treatment area, including the amount (intensity) of transmitted waves that pass through the tooth or bone being treated. As such, even in circumstances where ultrasound emitters may be provided on both sides of a tooth simultaneously, interference would likely be created inside the bone or tooth, affecting treatment results and leading to unpredictable treatment outcomes.

Moreover, current ultrasound devices, lack the ability to monitor and measure the quality of contact (coupling) between ultrasound emitters and the dental tissue to be treated. This absence of a monitoring ability results in a user not knowing when the device is improperly positioned or not functioning properly.

Control and regulation of ultrasound emission, simultaneous feedback, and monitoring of ultrasound emission and the coupling of the emitters to dental tissue, may provide means of determining and varying the treatment protocol for individual patients depending upon the thickness/density/shape of their individual treatment area. It is known that different thicknesses will necessitate different propagation paths for the ultrasound waves, which can affect the intensity of the waves received at the treatment area due to internal interference and absorption.

Therefore, there is a need for an ultrasound device and method for use of ultrasound that is easy and comfortable for patients to use, and that provides improved control and regulation means (including feedback means) for delivering an effective and accurate intensity of ultrasound to specific treatment areas. Such a device or method for use of ultrasound may be applicable for a variety of dental treatments, including, but not limited to: improved jaw bone and alveolar bone remodeling; improved healing following oral surgery or dental implanting, acceleration of orthodontic tooth movement; acceleration of tooth root remodeling; repair of tooth root resorption; acceleration of repair to jaw and alveolar bone fractures due to wisdom teeth extraction; treatment of tooth sensitivity at the root or crown level; reduction of gingiva infections, and improved healing of gingivitis and periodontitis, including healing after gingival flap surgery (a procedure used to treat periodontitis) and reduce pain or inflammation associated with oral surgery.

SUMMARY

Devices and methods for ultrasonic dental treatment are described, wherein the device and method may provide an intra-oral attachment having a flexible array of cooperative ultrasound transducers. The array can contain individual ultrasonic transducers that can perform both functions of emitting and sensing. The transducer emitters and transducer sensors can have the ability to interchange their functions, and emission from each transducer can be independently controlled by an external source controller. The transducers can cooperate in providing an ultrasound treatment. More specifically, an ultrasound system is provided comprising: an ultrasound transducer sensor array operable to emit or sense ultrasound, wherein the timing and intensity of emission may be controlled by an electronic controller based on a feedback signal from the sensors, a controller operatively coupled to the sensors and emitters and operable to transmit the feedback signal from the sensors and emitters to the controller; and a housing for carrying the transducer arrays and to position the sensor and the emitter arrays proximate the treatment area is provided. In addition the ultrasound system can also have the ability to sense coupling to a treatment tissue. This ability to sense proper coupling can improve the efficacy of the treatment.

Broadly stated, in some embodiments, a system is provided for use in emitting ultrasound to a dental area, the system comprising: an intra-oral dental attachment for providing ultrasound emissions to the dental area; the dental attachment comprising at least one flexible array of cooperative ultrasound transducers for emitting ultrasound and sensing at least one stimulus, and a matching layer disposed between the at least one flexible array and the dental area; and external controlling means for controlling the ultrasound emissions, the external controlling means being in communication with the dental attachment.

Broadly stated, in some embodiments, an intra-oral dental attachment for an ultrasound system is provided comprising: at least one flexible array of cooperative ultrasound transducers for emitting ultrasound and sensing at least one stimulus; a matching layer disposed between the at least one flexible array and a dental area; and a housing for containing the at least one flexible array and the matching layer, where the housing positions the at least one flexible array of ultrasound transducers in a manner to provide ultrasound emissions to the dental area.

Broadly stated, in some embodiments, a method of ultrasound dental treatment is provided comprising: providing an ultrasound dental system for dental treatment; applying ultrasound to a dental treatment area; sensing at least one stimulus; providing feedback based on the sensing; and adjusting application of ultrasound in response to the feedback; whereby a dental condition is treated.

Broadly stated, in some embodiments, a method of accelerating orthodontic treatment using ultrasound is provided, the method comprising the steps of: providing an ultrasound dental system for accelerating orthodontic treatment; applying ultrasound to a dental treatment area; sensing at least one stimulus; providing feedback based on the sensing; and adjusting application of ultrasound in response to the feedback; whereby an orthodontic treatment is accelerated.

DETAILED DESCRIPTION

Ultrasonic methods and devices for dental treatment are described. The methods and devices can be used to replace, prevent, enhance, or accelerate treatments of tooth roots, tooth crowns, periodontal ligaments, alveolar bones and jaw bones. In addition, the methods and devices can be used to improve (increase) the speed and success of other dental treatments such as dental implants osseointegration, healing of alveolar bone fractures due to extractions, alveolar bone modifications (remodeling) due to orthodontic appliances, or periodontal treatments.

Figure 1:
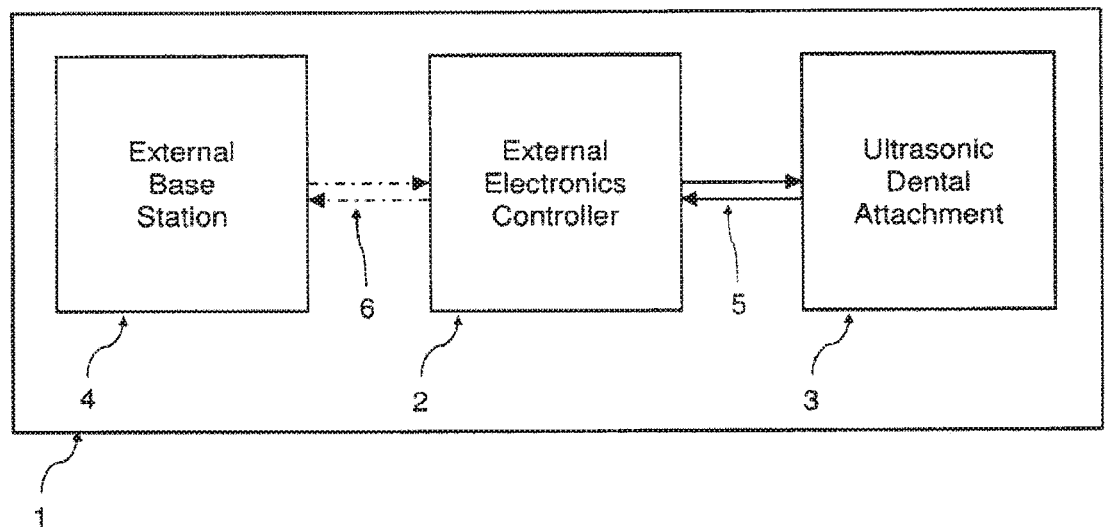
FIG. 1 is a block diagram of an embodiment of an ultrasonic dental system.

Referring now to FIG. 1, ultrasonic dental system 1 can include an external electronic controller 2, an ultrasonic dental attachment 3, and an external base station 4. External base station 4 can be a personal computer that can connect to the external electronic controller 2 though temporary, bidirectional communication, connection 6. Temporary connection 6 can be made through a wired means (for example, a cable) or a wireless means (for example, radio, infrared, or magnetic). External base station 4 can use a software application to interact with the external electronic controller 2.

External base station 4 can be used to program the ultrasonic dental system 1, download and read recorded treatment data and ensure treatment compliance, service or repair ultrasonic dental system 1, or charge the battery of external electronics controller 2 for instance by providing electrical power from the USB port of the personal computer. Battery of external electronics controller 2 could also be charged by means of a plug-in adapter (not shown).

External electronic controller 2 can be connected to ultrasonic dental attachment 3 through a fixed, bidirectional communication, connection 5. Fixed connection 5 can be a flexible multi wire cable.

Ultrasonic dental system 1 can also include a storage/travel box (not shown) to store ultrasonic dental attachment 3. The storage/travel box can also include a tray and solution for cleaning, disinfection and storage.

Figure 2:
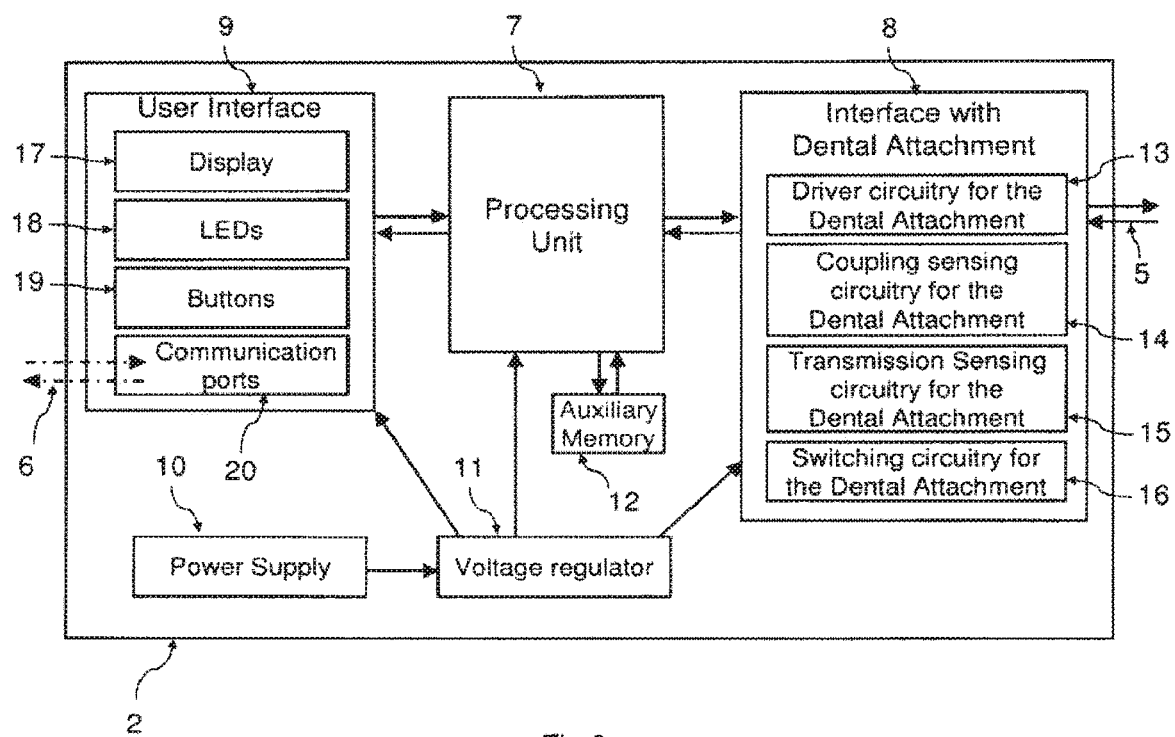
FIG. 2 is a block diagram of an embodiment of an external electronics controller of the system shown in FIG. 1.

Referring now to FIG. 2, external electronics controller 2 can be made using off-the-shelf electronic components, custom designed printed circuit board(s), and custom developed firmware. External electronics controller 2 can include a processing unit 7, a dental attachment interface 8, a user interface 9, a power supply 10, and a voltage regulator 11.

Processing unit 7 can be microcontroller such as an AVR 8-bit microcontroller, for example ATmega 2560, and can also include auxiliary memory 12. Interface 8 can connect external electronics controller 2 to ultrasonic dental attachment 3 through connection 5. Interface 8 can also include driver circuitry 13, coupling sensing circuitry 14, transmission sensing circuitry 15, and switching circuitry 16, for ultrasonic dental attachment 3. User interface 9 can include a display or touch screen 17, light emitting diodes (LEDs) 18, user buttons 19, and one or more communication ports 20. Communication ports 20 can be connected with the external base station 4 through temporary connection 6. Power supply 10 can be a battery (rechargeable or not-rechargeable), a charger for the battery, or a wall plug-in electric adapter. Communication ports 20 can also include charging features for power supply 10.

External electronic controller 2 can connect wirelessly or wired to another electronic device such as smart phone (not shown). The smart phone may act as some of the components of the external electronic controller 2 such as the user interface 9. In this case the external electronic controller 2 could be a module that attaches to the smart phone for example, and the smart phone can use an application software program to power and control the external electronic controller 2 which can control the ultrasonic dental attachment 3.

Referring now to FIGS. 3A, 3B, 3C, 3D, 4A, and 4B, ultrasonic dental attachment 3 can include interior ultrasound transducers 23 on the lingual side of a patients teeth 22 and exterior ultrasound transducers 24 on the buccal side of teeth 22. There can be sixteen teeth on each dental arch (mandible and maxilla) and there can be one interior transducer 23 on the lingual side of each tooth 22. In some embodiments one transducer can cover more than one tooth.

In some embodiments, more than one transducer can cover the buccal side of a tooth and/or the lingual side of a tooth. In some embodiments, not all teeth are covered. Sixteen interior transducers 23 on the lingual side of each dental arch can form a flexible array of transducers. In some embodiments, this array can be linear. In some embodiments, the array can comprise cooperative ultrasound transducers which can cooperate during ultrasound treatment. There can be one exterior transducer 24 on the buccal side of each tooth 22 and there can be sixteen exterior transducers 24 on the buccal side of each dental arch forming a flexible array of transducers. In some embodiments, this array can be linear. Flexible enclosure 25 can encase transducers 23, 24 and can cover the crown and root of the tooth. Flexible enclosure 25 can be made of plastic polymers such as polypropylene, copolyester or ethyl vinyl acetate (EVA). In one embodiment, two separate ultrasonic dental attachments 3 can be used interchangeably or simultaneously for the mandible and maxilla.

Figure 3A:
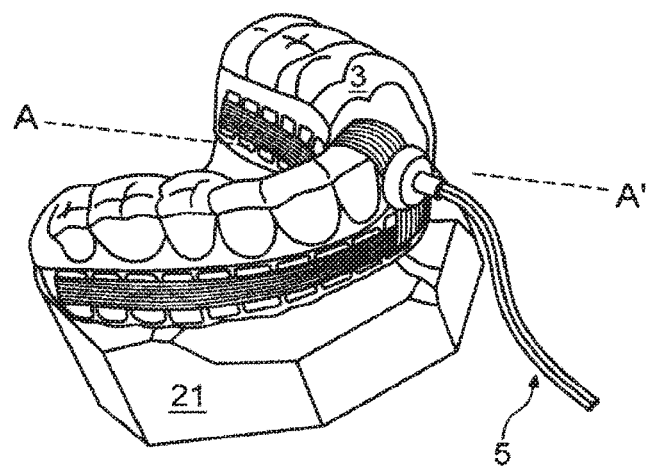
FIG. 3A is a perspective view of an embodiment of an ultrasonic dental attachment with an embedded connector placed on a dental cast.
Figure 3B:
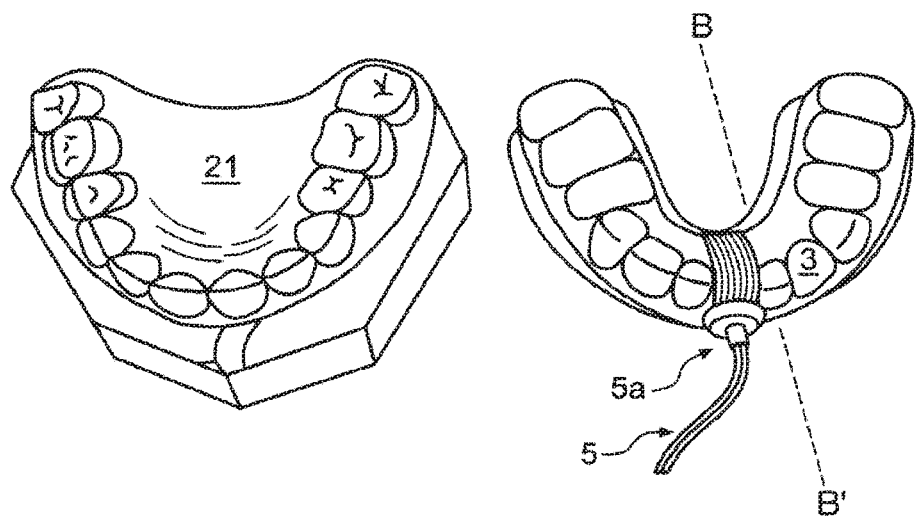
FIG. 3B is a top view of an embodiment of the ultrasonic dental attachment of FIG. 3A placed beside the dental cast.
Figure 3C:
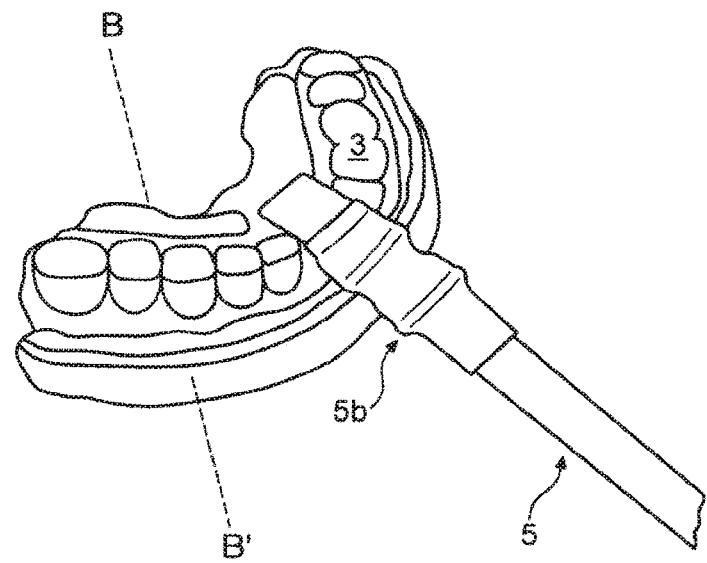
FIG. 3C is a perspective view of an embodiment of the ultrasonic dental attachment with an external connector.
Figure 3D:
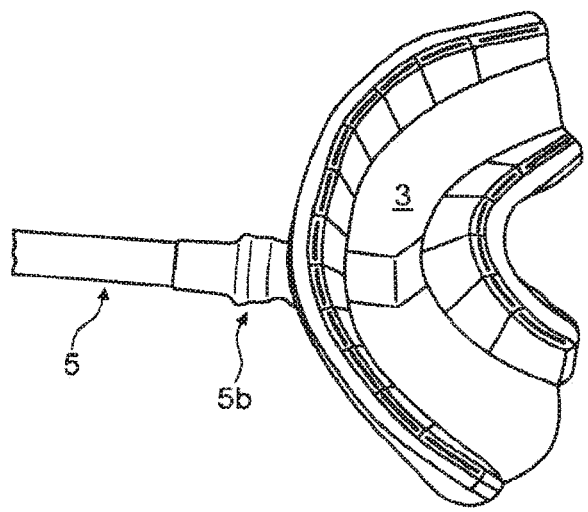
FIG. 3D is a bottom view of an embodiment of the ultrasonic dental attachment with an external connector.
Figure 3E:
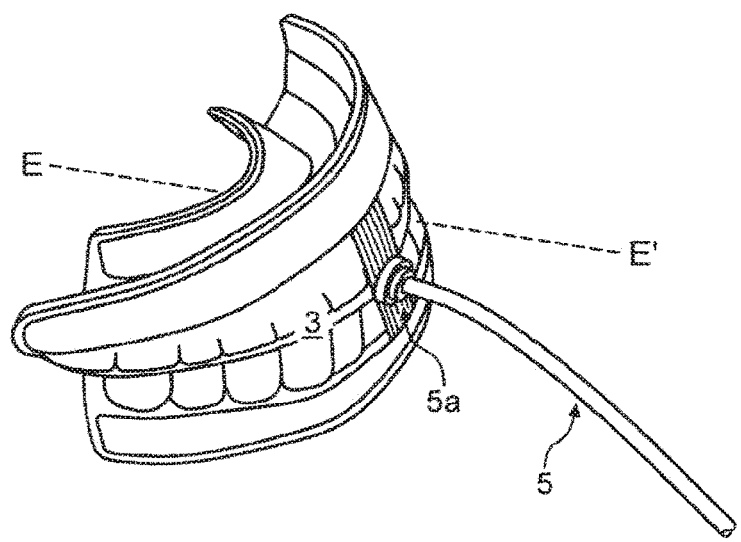
FIG. 3E is a perspective view of an embodiment of an ultrasonic dental attachment for the treatment of both dental arches.
Figure 4A:
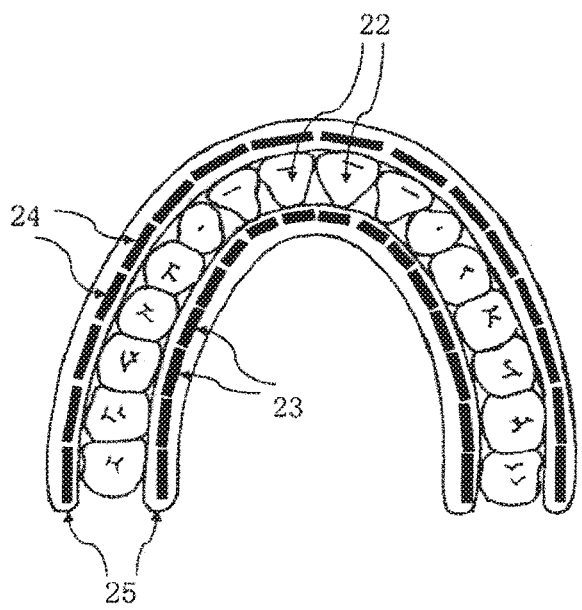
FIG. 4A is a horizontal cross-section view of the ultrasonic dental attachment shown in FIG. 3A through horizontal plane AA'.
Figure 4B:
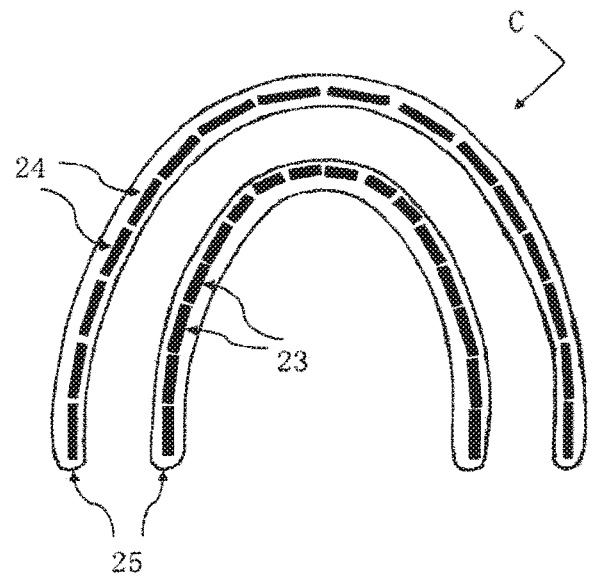
FIG. 4B is a horizontal cross-section view of the ultrasonic dental attachment shown in FIG. 3B through horizontal plane BB'.

Referring now to FIG. 3E, in another embodiment, two arches (one for mandible and one for maxilla) can be formed together into an ultrasonic dental attachment 3 that can treat both dental arches. As illustrated in FIG. 3E, ultrasonic dental attachment 3 can contain four flexible arrays of ultrasound transducers 23, 24: one array for maxillary buccal side, one for the maxillary lingual side, one for the mandible buccal side, and one for mandible lingual side. The ultrasonic dental attachment 3 can have orifices in the occlusion (bite section) of the dental attachment 3 to allow patient breathing.

Dental cast 21 is used for illustrating how the ultrasonic dental attachment 3 can fit on patient teeth 22. Ultrasonic dental attachment 3 can be similar to a mouthguard that can be heated in hot water and when bitten by a user can be fixed into a shape which follows the shape of the user's teeth. If a new shape of the ultrasonic dental attachment 3 is required (for instance in the case of orthodontic treatment where the teeth can change their position), then the patient can reheat the ultrasonic dental attachment 3 in hot water and bite it again to imprint the new shape or positions of the teeth 22. Professional alignment or adjustment of the position of the device is not necessarily required. The patient can bite down on ultrasonic dental attachment 3 in order to keep it positioned well on the teeth 22 during treatment and ensure the placement is consistent with each use.

Connection 5 is shown as a cable which can connect ultrasonic dental attachment 3 to external electronics controller 2. In some embodiments, connection 5 can include wires and embedded connector 5a water-sealed inside the ultrasonic dental attachment (FIG. 3A, B, E), or external connector 5b (FIGS. 3C and 3D) as an extension of the ultrasonic dental attachment 3. Connectors 5a or 5b can connect transducers 23, 24 from ultrasonic dental attachment 3 to the external electronics controller 2 as desired through connection cable 5.

In addition, the connectors 5a and 5b can be permanently attached or can be disconnected when cleaning, replacing or servicing of intra-oral attachment 3 is required.

Figures 5A, 5B:
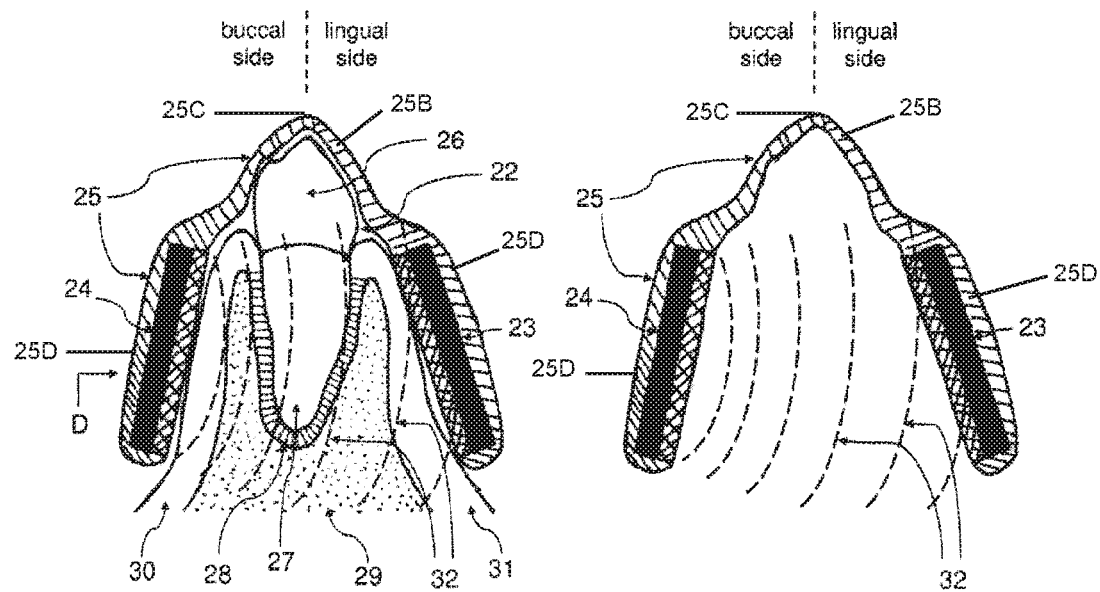
FIG. 5A is a vertical cross-section view of the ultrasonic dental attachment shown in FIG. 3A through points AA'.
FIG. 5B is a vertical cross-section view of the ultrasonic dental attachment shown in FIG. 3B through points BB'.

Referring now to FIGS. 5A and 5B, tooth 22 can include crown 26 and root 27.

Tooth 22 can be connected through periodontal ligaments 28 to alveolar bone 29. Gums, or gingiva 30,31, can envelope alveolar bone 29 on the buccal side 30 and on the lingual side 31 of tooth 22.

In one embodiment, ultrasound waves 32 can be propagated from the buccal side transducer 24 through flexible enclosure 25, buccal side gums 30, alveolar bone 29, periodontal ligaments 28, tooth root 27, and can continue propagation through periodontal ligaments 28, alveolar bone 29, lingual side gums 31, flexible enclosure 25 on the lingual side of tooth 22 and finally can enter the lingual transducer 23 where ultrasound wave 32 can be converted into an electric signal. In some embodiments, flexible enclosure (housing) 25 can comprise an array-to-tooth-root positioning structure 25B which can comprise a base portion 25C for being positioned along an occlusal plane of a patient to be treated, and a flange 25D extending away from base portion 25C and for being positioned along and proximate the length of the tooth root 27 and gum tissue 30, 31, in order to position the at least one flexible array of ultrasound transducers 23, 24. For instance, first and second flanges 25D may extend away from base portion 25C for respectively being positioned along and proximate opposite sides of the length of the tooth root 27 as shown in the embodiments of FIGS. 5A-5J. As another example, first and second flanges 25D may extend away from base portion 25C for respectively being positioned along and proximate the lengths of tooth roots 27 from both dental arches (maxilla and mandible) as shown in FIGS. 5M-5P. As a further example, first, second, third and fourth flanges 25D may extend away from base portion 25C for respectively being positioned along and proximate opposite sides of the lengths of tooth roots 27 from both dental arches (maxilla and mandible) as shown in the embodiments of FIGS. 5K-5L.

Ultrasonic dental attachment 3 can use coatings or layers between gums 30, 31 and transducers 23, 24 that can behave as antireflection layers for the ultrasound waves 32 at an operating frequency. The thickness of the coatings can be an odd multiple of quarter wavelengths of an ultrasound wave 32 in that material. This thickness can allow improved coupling of ultrasound waves 32 from the emitter to the tissues and from the tissues to the sensor and also can reduce the reflections back to the emitter or sensor which can cause noise in ultrasonic dental system 1 and wave interference that can affect treatment outcomes.

Flexible enclosure 25 can be made of flexible materials such as polypropylene, copolyester or ethyl vinyl acetate (EVA) which can be thermally formed, injection molded, deposited, or applied over and around transducers 23, 24 in order to seal them from the external factors such as the saliva from the patient or humidity from the environment. Such layers of flexible materials can have thickness of less than 1 mm while maintaining good strength and sealant properties.

In this example, buccal side transducer 24 can emit ultrasonic waves, while the lingual side transducer 23 can receive and sense ultrasonic waves 32, although it would be appreciated that the opposite could also occur. In this scenario, transducer 24 works as an emitter and transducer 23 as a transmission sensor. In order to expose the tooth root 27 or crown 26 to uniform ultrasonic treatment (uniform ultrasonic intensity), the transducers 23, 24 from the buccal and lingual side can interchange their dual function of emitting and sensing. For instance, during a further step in treatment, transducer 23 can emit ultrasound waves 32 and transducer 24 can sense the transmitted ultrasound waves 32. In this way ultrasonic waves can equally expose tooth 22 from both sides.

When multiple ultrasound emitters are used at the same time in proximity to each other, wave interference can occur which can reduce the dental treatment outcome or can also cause tissue damage. The amplitude and location of wave interference patterns can be difficult to predict and control as each patient has a unique dental structure. Ultrasonic dental system 1 can be configured so that transducers 23, 24 will not emit ultrasound waves 32 at the same time. As such, ultrasonic dental system 1 can avoid the interference of the ultrasonic waves 32 inside tissues 27, 28, 29, 30, 31.

In one embodiment, transducer 23, 24 can cover the entire length (or a large portion) of root 28, from the gum-crown interface to the tip of the root. By using a transducer that covers the root 28, it can be possible to treat dental problems located at any point of root 28 including its tip, or treat the alveolar bone 29 all around the root and its tip. Applications can include healing dental implants, root resorption, periodontitis, and accelerating alveolar bone remodeling.

The area and shape of transducers 23, 24 can vary from tooth to tooth and from buccal side to the lingual side of a tooth 22. Transducers 23, 24 can have different shapes (rectangular, trapezoids, ovals, circular, etc), with different widths, heights, or radii. In some embodiments, the width of transducers 23, 24 can be similar with the width of a tooth crown 26, while the height can be similar with the length of the root 27. As the width of tooth 22 and the length of root 27 varies from tooth to tooth (for example incisors have a smaller crown 26 width but a longer root 27 than a molar), transducers 23, 24 can have different widths and heights.

Figures 5C, 5D:
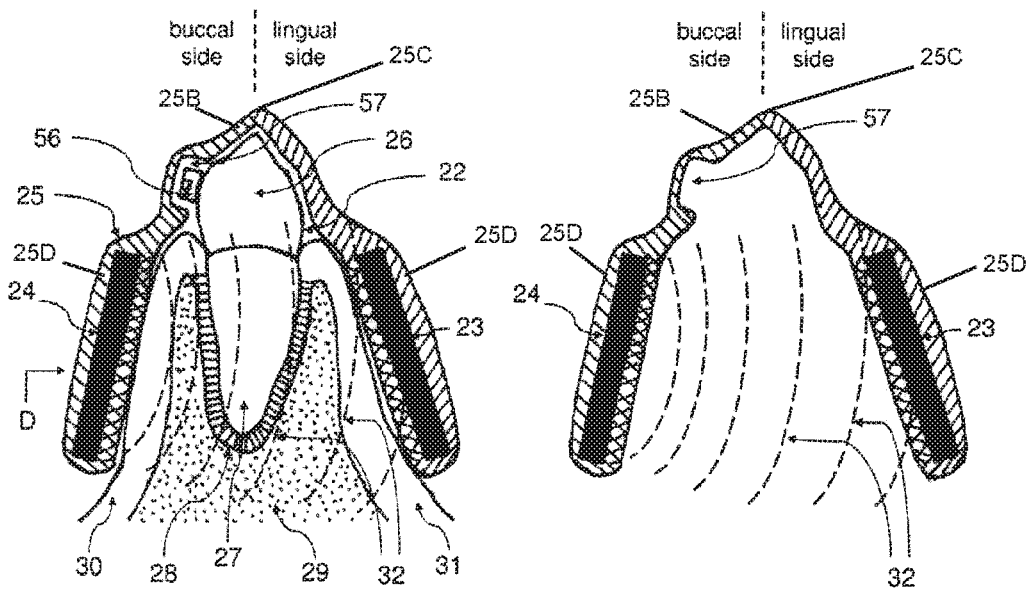
FIG. 5C is a vertical cross-section view of the ultrasonic dental attachment shown in FIG. 3A through points AA' where the ultrasonic dental attachment has been modified to accommodate wire braces.
FIG. 5D is a vertical cross-section view of the ultrasonic dental attachment shown in FIG. 3B through points BB' where the ultrasonic dental attachment has been modified to accommodate wire braces.

Referring now to FIGS. 5C and 5D, a further embodiment of ultrasonic dental attachment 3 can also be configured to accommodate orthodontic braces 56 that are on a patient's tooth 22. Ultrasonic dental attachment 3 can have a cavity 57 in flexible enclosure 25 to allow the brackets and wires from the orthodontic braces to fit inside. Alternatively, cavity 57 can be an orifice through the flexible enclosure 25. A patient can wear both braces and ultrasonic dental attachment 3 at the same time. In one embodiment, ultrasonic dental attachment 3 does not contact the brace brackets or the brace wires as to not affect the way the orthodontic forces are applied by the orthodontic braces to the tooth. Where ultrasonic dental attachment 3 can be made of a soft material and can contact crown 26 such that uniform force can be applied in all directions as to not influence the orthodontic brace forces.

In FIGS. 5C and 5D the orthodontic braces are illustratively located on the buccal side of the teeth however, the braces can also be located on the lingual side of the teeth, as required on the particular patient treatment and type of braces chosen. As a result, cavity 57 can also be located on the lingual side or on both sides of flexible enclosure 25, as required to accommodate the location of the braces.

Figures 5E, 5F:
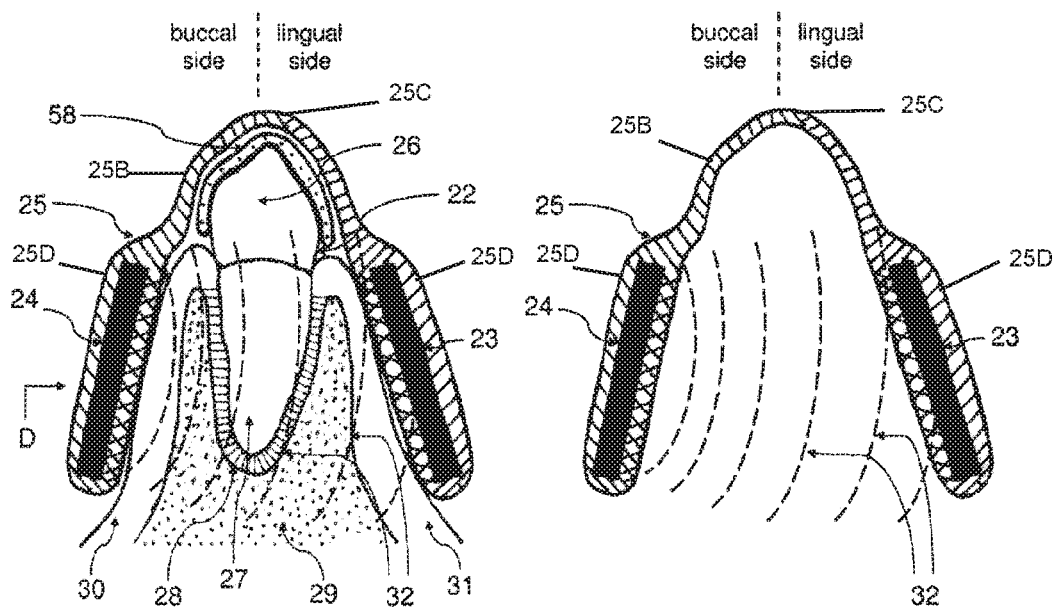
FIG. 5E is a vertical cross-section view of the ultrasonic dental attachment shown in FIG. 3A through points AA' where the ultrasonic dental attachment has been modified to accommodate a clear orthodontic aligner or retainer.
FIG. 5F is a vertical cross-section view of the ultrasonic dental attachment shown in FIG. 3B through points BB' where the ultrasonic dental attachment has been modified to accommodate a clear orthodontic aligner or retainer.

Referring now to FIGS. 5E and 5F, a further embodiment of ultrasonic dental attachment 3 can be designed to be used with clear aligners or retainers 58. A larger gap between flexible enclosure 25 and tooth crown 26 can allow aligners or retainers 58 to fit inside the ultrasound dental attachment 3.

Figures 5G, 5H:
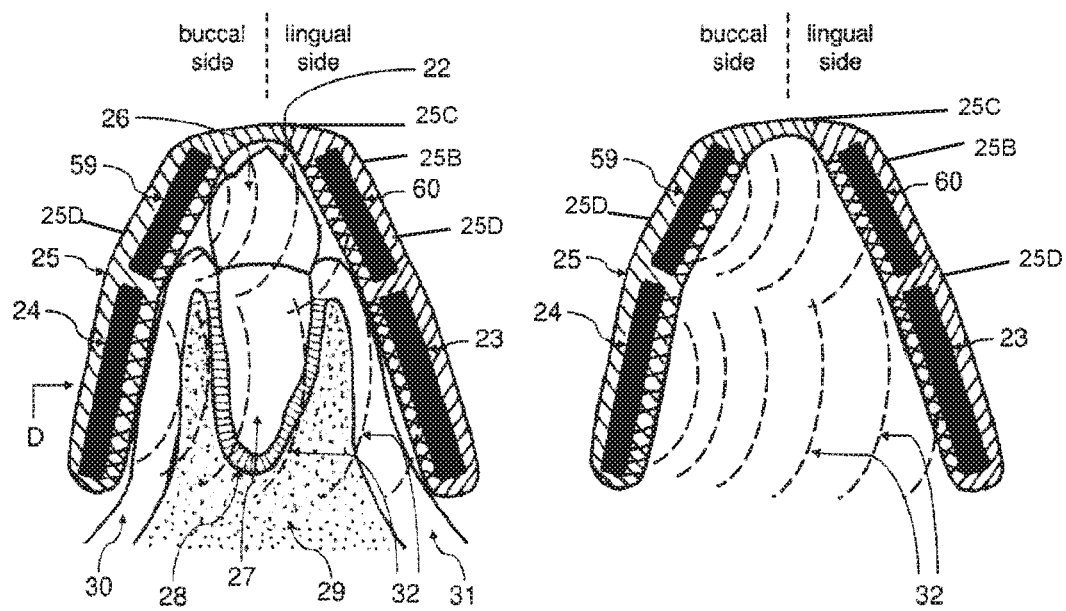
FIG. 5G is a vertical cross-section view of the ultrasonic dental attachment shown in FIG. 3A through points AA' where the ultrasonic dental attachment has been modified for treatment of both a tooth crown and a tooth root.
FIG. 5H is a vertical cross-section view of the ultrasonic dental attachment shown in FIG. 3B through points BB' where the ultrasonic dental attachment has been modified for treatment of both a tooth crown and a tooth root.

Referring now to FIGS. 5G and 5H, a further embodiment of ultrasonic dental attachment 3 can be designed to treat both tooth root 27 and crown 26. A second array of emitters and a second array of sensors can be in parallel above the emitters and sensors which cover the length of root 27 and which will cover the crown 26 partially or totally. Transducers 24 and 59 can be placed on the buccal side and transducers 23 and 60 can be placed on the lingual side. Ultrasound transducers 59 and 60 can be used for the treatment of tooth crown afflictions such as stimulating new dentine formation to help repair deep cavities or to treat tooth sensitivity to cold, hot, or sweet.

In alternative embodiments, transducers 23, 24 can also cover the length of the crown 26 of tooth 22 (transducers 23, 24 could cover both the root and the crown at the same time, in their entirety or only portions thereof). By using an ultrasound transducer that covers also the crown 26, ultrasonic dental system 1 can treat crown problems such as deep cavities that can require ultrasound stimulation to enhance the pre-dentine formation from inside the tooth to potentially avoid a root canal. By exposing the entire tooth 22 (root 27 and crown 26) to ultrasonic waves ultrasonic dental system 1 can treat the entire tooth surface for sensitivity to cold, hot, or sweet, by stimulating the entire tooth interior which can lead to depositing of additional dentin in the areas that cause the sensitivity.

Ultrasonic Dental System can also help treat dental afflictions located at the gum line, such as reducing gingiva infections, inflammation or pain, or helping accelerate healing after gingival surgical interventions (such as gingival flap surgery, dental implant or surgical tooth extractions)

Figures 5I, 5J:
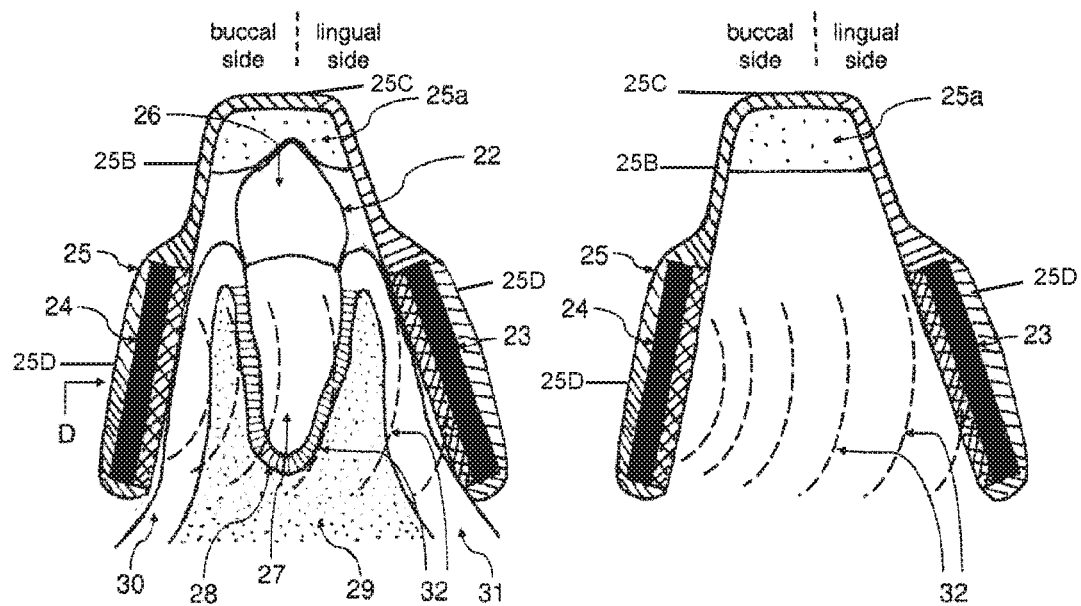
FIG. 5I is a vertical cross-section view of the ultrasonic dental attachment shown in FIG. 3A through points AA' where the ultrasonic dental attachment has been modified to accommodate a soft bite pad.
FIG. 5J is a vertical cross-section view of the ultrasonic dental attachment shown in FIG. 3B through points BB' where the ultrasonic dental attachment has been modified to accommodate a soft bite pad.
Figures 5K, 5L:
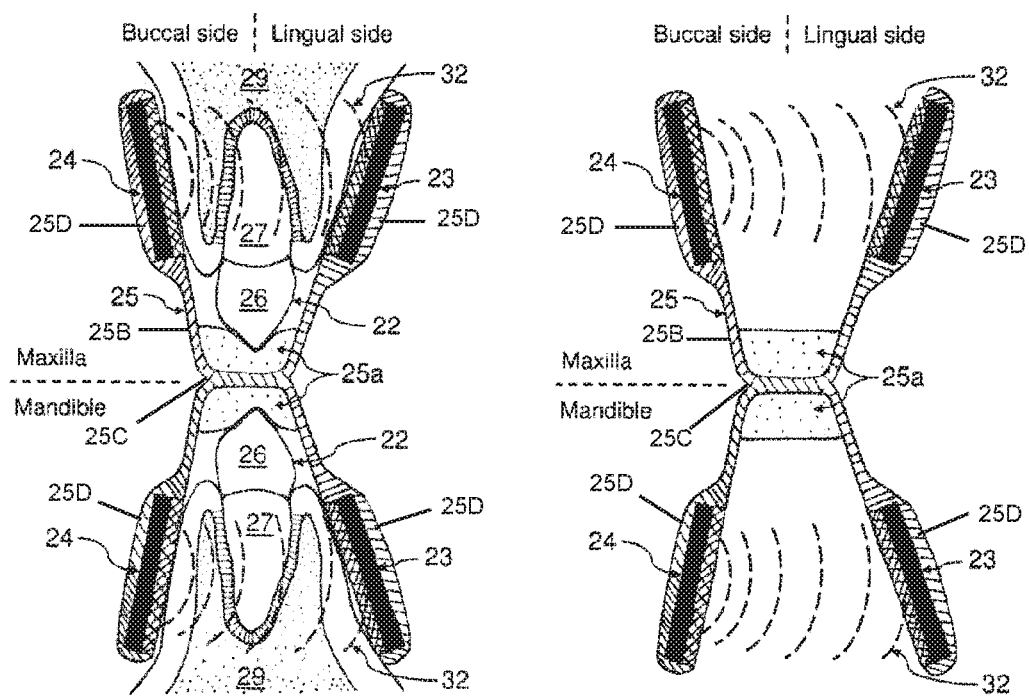
FIG. 5K is a vertical cross section view of the ultrasonic dental attachment shown in FIG. 3E through points EE and placed over teeth, where the ultrasonic dental attachment has been modified to fit both dental arches (maxilla and mandible)
FIG. 5L is a vertical cross section view of the ultrasonic dental attachment shown in FIG. 5K when not placed over teeth.

Referring now to FIGS. 5I and 5J, a further embodiment of ultrasonic dental attachment 3 can be designed to have a general form of a dental tray. In some embodiments, the interior of the tray (facing tooth crown 26) can be filled with soft bite pad 25a which can be made of a malleable material. As an example, soft bite pad 25a can be made of silicone. Therefore when the patient bites attachment 3, soft bite pad 25a can reshape and accommodate tooth crowns 26. If the position of the teeth change over time (such as during orthodontic treatment), soft bite pad 25a can allow continuous fit over tooth crowns 26. An embodiment of the ultrasonic dental attachment 3 can accommodate any type of orthodontic appliance (for example, wire braces and clear orthodontic aligners). As illustrated in FIG. 5J, soft bite pad 25a can recover its original shape when not bitten.

Referring now to FIGS. 5K and 5L, in some further embodiments, ultrasonic dental attachment 3 can be designed to fit both dental arches (maxilla and mandible). Some embodiments can deliver ultrasonic treatment selectively to tooth roots 27 from both dental arches (maxilla and mandible) and from both lingual and buccal directions as desired, while using a single external electronics controller 2.

Figure 5M:
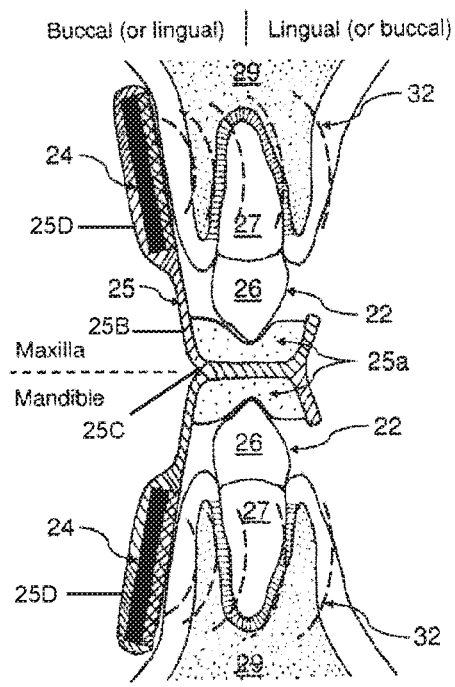
FIG. 5M is a vertical cross section view of the ultrasonic dental attachment shown in FIG. 5K modified to emit ultrasound from only one of either lingual or buccal sides only.
Figure 5N:
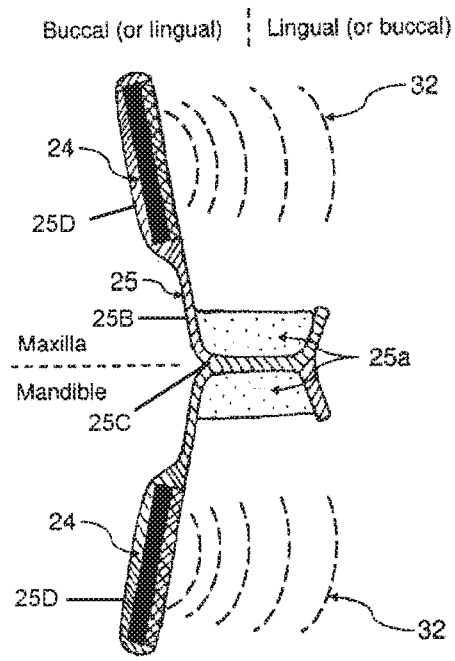
FIG. 5N is a vertical cross section view of the ultrasonic dental attachment shown in FIG. 5M when not placed over teeth.

Referring now to FIGS. 5M and 5N, some embodiments of ultrasonic dental attachment 3 can be designed to fit both dental arches (maxilla and mandible), and deliver the ultrasonic treatment selectively to tooth roots 27 from both dental arches (maxilla and mandible) from one direction only (lingual or buccal) using a single external electronics controller 2.

Figure 5O:
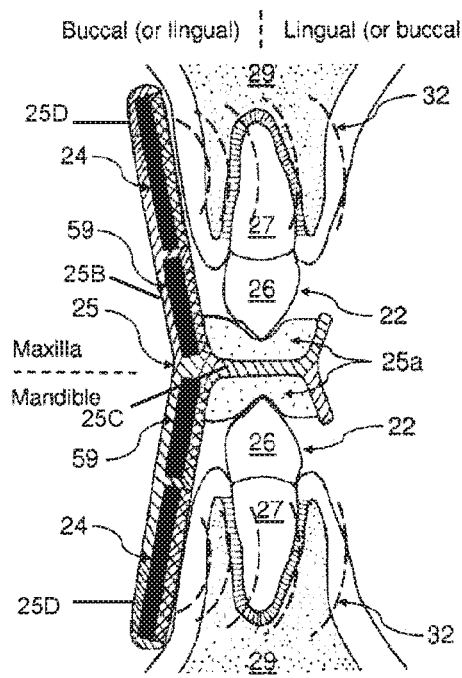
FIG. 5O is a vertical cross section view of the ultrasonic dental attachment shown in FIG. 5M, modified to emit ultrasound to both teeth roots and teeth crowns.
Figure 5P:
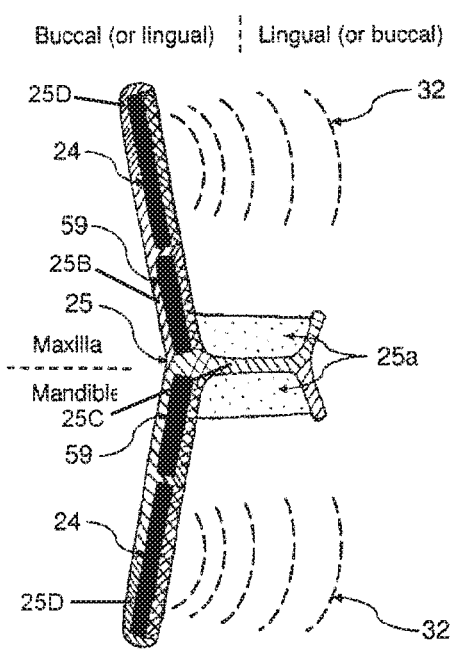
FIG. 5P is a vertical cross section view of the ultrasonic dental attachment shown in FIG. 5O when not placed over teeth.

Referring now to FIGS. 5O and 5P, some further embodiments of ultrasonic dental attachment 3 can be designed to fit both dental arches (maxilla and mandible), deliver the ultrasonic treatment selectively to tooth roots 27 and tooth crowns 26 from both dental arches (maxilla and mandible) from one direction only (lingual or buccal), using a single external electronics controller 2.

FIGS. 5K, 5L, 5M, 5N, 5O and 5P illustrate examples of ultrasonic dental attachments that can treat both dental arches (maxilla and mandible): from both lingual and buccal directions (FIGS. 5K and 5L), from one direction only (FIGS. 5M and 5N), and can also treat tooth crowns (FIGS. 5O and 5P). The embodiments in FIGS. 5M, 5N, 5O and 5P can be made to attach and emit ultrasound to the lingual side of the teeth or to the buccal side of the teeth, as required for treatment. For instance, people wearing customized orthodontic appliances such as space closing springs or temporary anchorage screws, some embodiments of the ultrasonic dental attachment may physically interfere with the springs or anchorage screws and it is desired to use an ultrasonic dental attachment that has the ultrasonic transducers on the side opposite of the springs or screws. In addition, FIGS. 5K, 5L, 5M, 5N, 5O and 5P illustrate examples where the soft bite pad 25a can be used, but orifices 57 (as shown in FIG. 5D) can also be used, or extra space for clear aligners 58 (as shown in FIG. 5E) could also be used, or a tighter fit as illustrated in FIG. 5A could also be used, or any combination of the above.

To allow for good coupling of the ultrasonic waves to teeth (crowns and gums), in some embodiments, a coupling agent can be applied to the tooth/gum contacting surface of ultrasonic dental attachment 3 when treatment is to be applied. In some embodiments, the coupling agent can be ultrasonic gel. In some embodiments, the coupling agent can be water or a water-soaked substrate. It would be understood by a person skilled in the art that any material which functions as a suitable coupling agent can be used.

In a further embodiment of ultrasonic dental attachment 3, soft membrane (not shown) can delimit transducers 23, 24. A membrane can also separate the area below gum and above gum, so ultrasonic dental attachment 3 can be used for whitening purpose where a whitening gel will be applied or injected separately only to cover the crown of the teeth. Further, in some embodiments, a membrane can be used to indicate the area for ultrasonic gel to be applied.

Figure 6A:
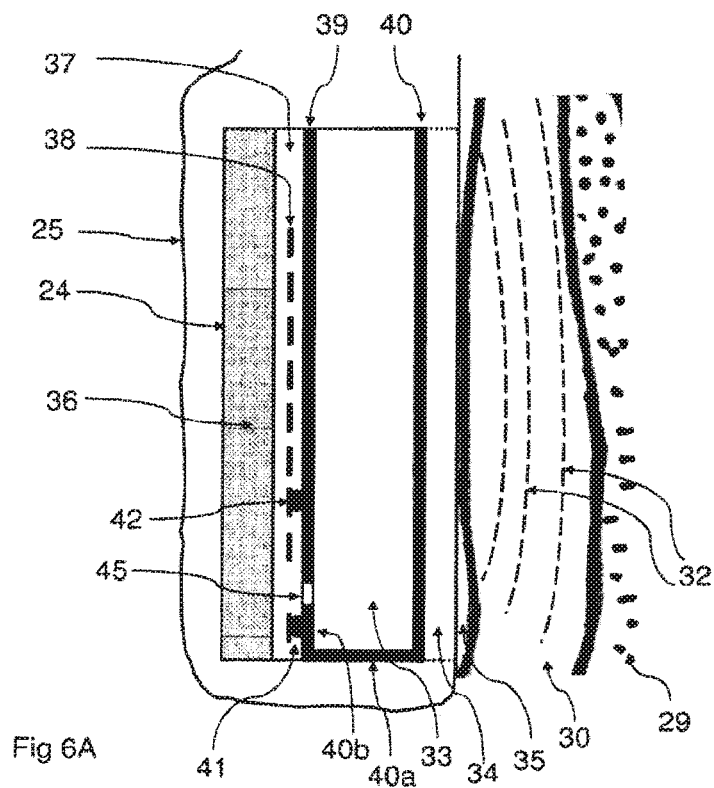
FIG. 6A is a cross section close-up view of an embodiment of an ultrasound transducer.

Referring now to FIG. 6A, a cross section of an embodiment of ultrasound transducer 24 which can emit ultrasound waves 32 is shown. Transducer 24 can include a piezoelectric material plate 33. Piezoelectric plate 33 can be made of piezoelectric materials such as PZT (Lead-Zirconate-Titanate), BaTiO3 (Barium Titanate) or PbNb2O6 (Lead Mataniobate). When piezoelectric materials containing potentially hazardous materials (such as lead) are utilized, piezoelectric plate 33 can be coated with a humidity/moisture indicator substance. In the event there is a saliva leaking into ultrasonic dental attachment 3, the indicator substance can change color thereby alerting a patient to stop using the device. The thickness of piezoelectric plate 33 can be constant and according to the acoustic velocity of the piezoelectric material from which transducers 23, 24 are made, and by the frequency at which transducers 23, 24 are operated at resonance. For example, to drive transducers 23, 24 at resonance, the thickness of piezoelectric plate 33 can be half a wavelength of the frequency of operation. For example, piezoelectric plate 33 made of PZT and resonant at 1.5 MHz can have a thickness in the order of 1.4 mm. Driving transducers 23, 24 at resonance can allow maximum power conversion efficiency from electrical power to ultrasonic power.

Ultrasonic dental attachment 3 can further include acoustic impedance matching layer 34 (which can be part of the overall device flexible enclosure 25) and air back layer 36. Transducer 24 can be glued or otherwise attached to acoustic impedance matching layer 34 in order to provide that there is no air gap in between. Air back layer 36 can be a foam layer (such foam tape, or sputtered or deposited foam or an air gap). The foam can be made of flexible material such as urethane and can have high air or neutral gas content. Foam tapes with thickness on the order of 1 mm or even less can be used in order to obtain a compact (thin) transducer structure. Air back layer 36 can also be created by applying a substance that can prevent flexible enclosure 25 material to stick to the back of the transducer 24. Due to the elastic force of flexible enclosure 25 material, when no glue is applied in between on transducer 24, a very thin gap can form. This gap can act as an air back reflector for the transducer 24.

Ultrasonic gel 35 can be used in-between acoustic impedance matching layer 34 and gum 30 which can allow a good coupling of ultrasonic waves 32 to the gums 30 and alveolar bone 29. Acoustic impedance matching layer 34 can have a thickness of odd multiples of quarter wavelengths of the ultrasound waves at the operation frequency in the material from which the impedance matching layer is made of. For example, the thickness can be a single quarter wavelength of ultrasonic waves 32 which can allow minimal absorption of the ultrasonic waves 32 when propagating through layer 34. For example, if acoustic impedance matching layer 34 is made of materials such as polypropylene, copolyester or ethyl vinyl acetate (EVA), then the thickness of layer 34 can be on the order of 0.3-0.5 mm. This thickness can vary with the material used and its parameters.

Matching layer 34 can be made of one material layer, or a combination of two or more layers of different materials. For instance, a first layer of a harder material like polypropylene or copolyester can be attached first to electrode 40 of transducer 33 in order to obtain a solid mechanical sealing, and a second layer of a softer material such as EVA or silicon can be attached to provide comfortable contact to gums 30 of patients. In this example, the thickness of both layers can be chosen to allow maximum transmission and minimum absorption. It would be understood by one skilled in the art that other materials or combinations of materials than the one mentioned above could also be used for the matching layer 34.

In some embodiments, a thin layer of water absorbent material such as foam of fabric could be attached permanently or temporarily to matching layer 34 in order to form a layer of water in-between matching layer 34 and gum 30. Such embodiments could operate without ultrasonic gel but would require a patient to imbibe the foam or fabric layer in water before use. The water absorbent layer can come pre-imbibed in an aqueous solution in some embodiments. The water absorbent layer can also have antibacterial properties or different flavors. Moreover, the water absorbent layer could be a disposable component that the patient can attach to the ultrasonic dental attachment 3 prior to use, and can discard it after application.

Ultrasonic dental attachment 3 can include a flexible cable 37 with parallel wire traces. Flexible cable 37 can be a flat flexible cable (FFC) or flexible printed circuit (FPC). Flexible cable 37 can contain individual wires 38 laminated between two dielectric films, where individual wires 38 can be flat metal conductors. The thickness of a FFC can be in the order of 0.5 mm while the thickness of a FPC can be in the order of 0.1 mm.

Ultrasonic dental attachment 3 can include a back electrode 39 and a front electrode 40 on the piezoelectric plate 33. Back electrode 39 can cover the majority of the back surface of the piezoelectric plate 33 with the exception of a gap 45 and a small area electrode 40b. Gap 45 between electrodes 39, 40b can allow electrical insulation between the two electrodes 39, 40b. Front electrode 40 can cover the entire front surface of piezoelectric plate 33, and can continue on the side (for example, on the bottom side) of plate 33 as electrode 40a and can cover a small area (for example, a corner) of the back surface of plate 33 as electrode 40b. Electrodes 40, 40a and 40b can be electrically connected. In this way both electrodes 39, 40 can be accessible on the same side (for example on the back side) of plate 33 to facilitate connection to flexible cable 37. One wire 38 of flexible cable 37 can connect to front electrode 40 by connecting to electrode 40b at electrical connection 41. A second wire 38 of flexible cable 37 can connect to back electrode 39 at electrical connection 42. Electrical connections 41 and 42 can be made by soldering or by conductive glue. A window in the insulation layer of the flexible cable 37 can be opened in order to allow the connection to be made between an individual conductor and the transducer electrode.

The total thickness of transducer 24 structure from gums 30 to the back of the flexible enclosure 25 can be in the order of 3-5 mm, depending of the materials used for manufacturing. This thickness can allow patient comfort, while still providing efficient transducer operation (for example, by having air back reflector 36 and acoustic impedance matching layer 34 on the front) and the treatment flexibility of emitting ultrasound waves 32 towards any or all teeth in a patient's mouth.

Figure 6B:
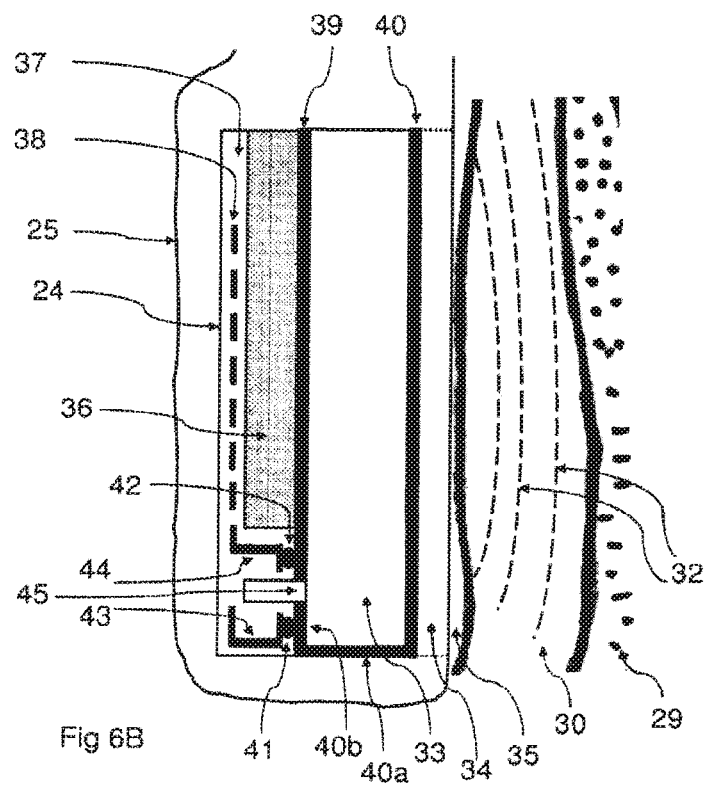
FIG. 6B is a cross section close-up view of a further embodiment of an ultrasound transducer.

Referring now to FIG. 6B, a cross section of a further embodiment of ultrasound transducer 24 which can emit ultrasound waves 32 is shown. In this example, air back layer 36 can be attached directly to back electrode 39 from back side of piezoelectric plate 33. Flexible cable 37 can be attached on top of air back layer 36. Lateral connectors 44 and 43 can run from flexible cable 37 in order to contact the flexible cable 37 to back electrode 39 and electrode 40b. Electrode 40b can be connected through electrode 40a to front electrode 40.

Figure 6C:
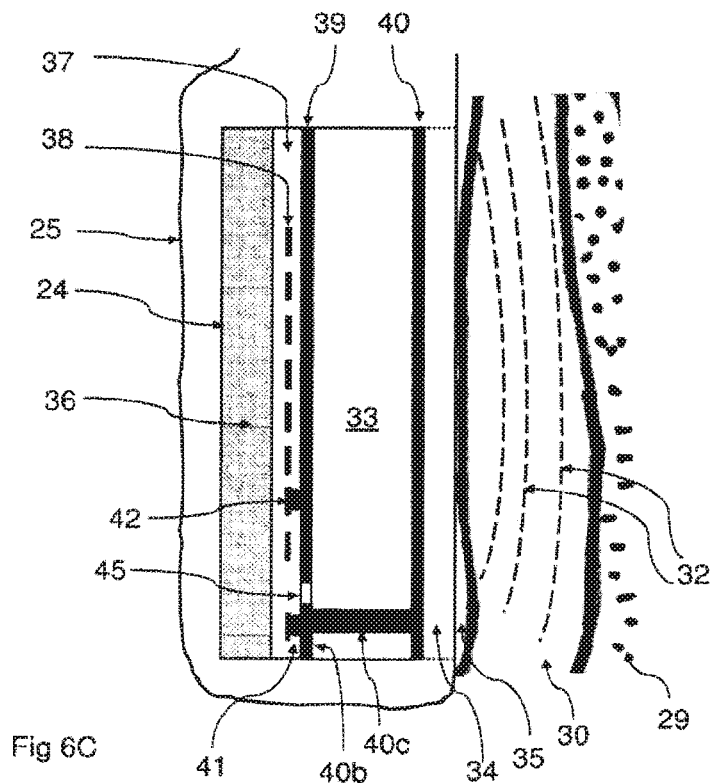
FIG. 6C is a cross section close-up view of a further embodiment of an ultrasound transducer.

Referring now to FIG. 6C, a cross section of a further embodiment of ultrasound transducer 24 which can emit ultrasound waves 32 is shown. In this example front electrode 40 can be electrically connected to the back side of piezoelectric plate 33 and electrode 40b by means of a through-hole via 40c. Through-hole 40c can be pre-made (pre-shaped) during transducer manufacturing, or drilled using laser machining. Through-hole 40c can be filled or plated with conductive material (for example by electroplating, soldering, riveting, or application of conductive paint or epoxies).

The cross section of transducers from buccal side 24 and lingual side 23 can be the same. Embodiments shown in FIGS. 6A, 6B, and 6C can be used for buccal transducers 24 as well as for lingual transducers 23, or a combination of the three embodiments can be used within ultrasonic dental attachment 3.

In the embodiments shown FIGS. 6A, 6B and 6C, piezoelectric material 33 can be replaced with a capacitive micromachined ultrasonic transducer (CMUT) array. In this case, air back layer 36 would not be required, as CMUT emits unidirectional.

Figure 7A:
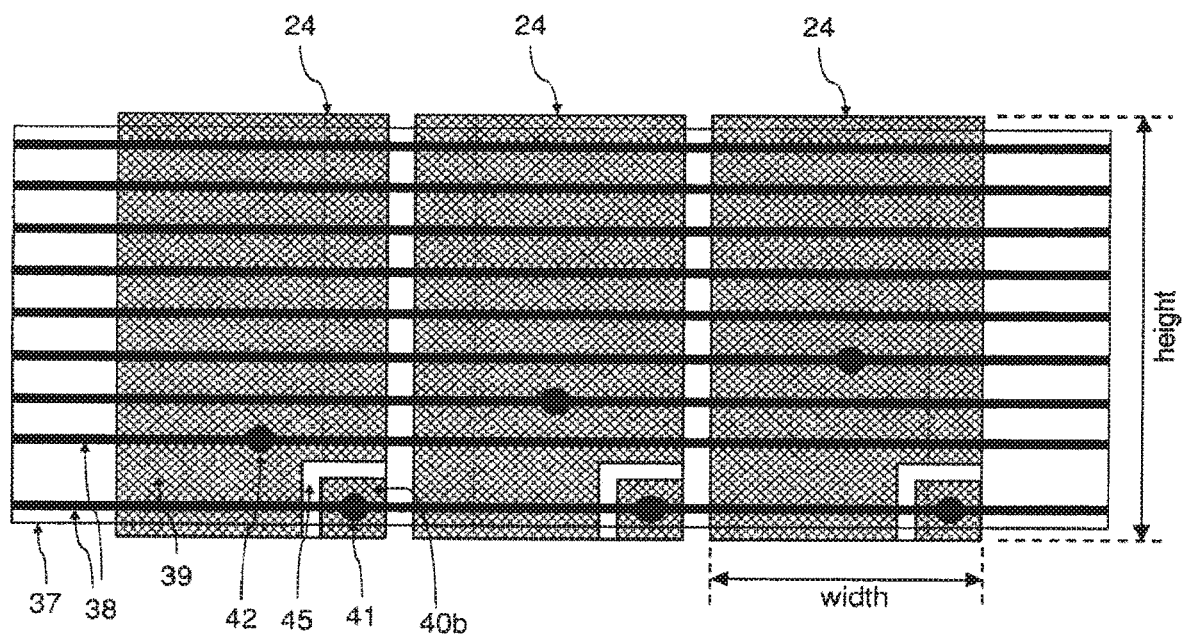
FIG. 7A is a partial rear view of an embodiment of an array of ultrasound transducers.

FIG. 7A illustrates an embodiment of an array of ultrasound transducers 24 viewed from the back of transducers 24 facing away from the gums 30. This embodiment illustrates the transducer structure of FIG. 6A where the flexible cable 37 can be located between the air back layer 36 and back electrode 39. FIG. 7A shows an array of transducers 24 which can be interconnected using flexible cable 37 with individual wires 38. Only three transducers 24 are illustrated for exemplification but it is understood that there can be several, for example sixteen, buccal transducers 24 which can be connected in this manner. This transducer array configuration can also apply to lingual transducers 23.

It would be understood that while air back layer 36 is not illustrated in FIG. 7A, this layer can be attached over flexible cable 37. Air back layer 26 can be cut in individual pieces to overlap the surface of each transducer 23 or 24, or be a long band that covers groups of transducers 23 or 24 or all transducers 23 or 24 of a flexible transducer array.

FIG. 7A shows the pattern of electrodes 39, 40b as seen on the back of piezoelectric plates 33. This electrode and connectivity configuration can allow easy connectivity while using a single electrode pattern for all transducers. Different electrode patterns for different transducers can be utilized for cases were custom designed devices need to be manufactured.

Transducers 24 can use a common wire to connect to electrode 40b which can be connected to front electrode 40 (as the ground electrode) at connection point 41 of each transducer. Possible placement of flexible cable 37 and individual wires 38 and connections to the electrodes 39 and 40b are shown. Connections 41, 42 can be made by soldering, or conductive glue or epoxy. This transducer configuration can also apply to lingual transducers 23.

Figure 7B:
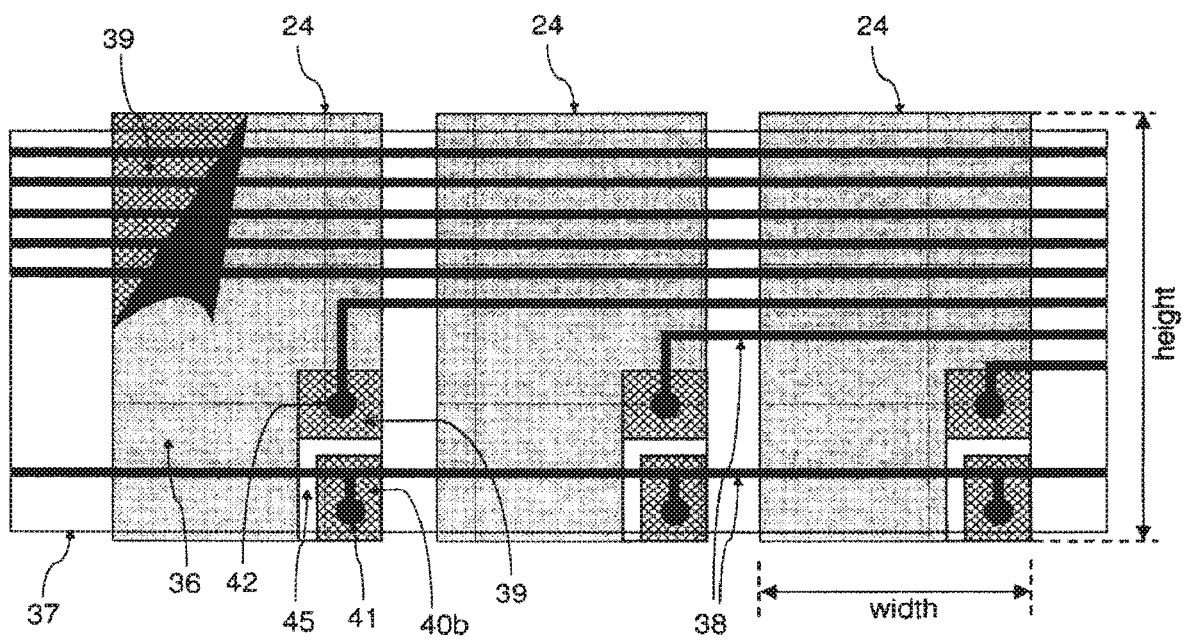
FIG. 7B is a partial rear view of a further embodiment of an array of ultrasound transducers.

Referring now to FIG. 7B, a further embodiment of an array of ultrasound transducers 23 or 24 is shown. FIG. 7B illustrates the transducer structure from FIG. 6B where air back layer 36 can be located between flexible cable 37 and back electrode 39. Air back layer 36 can be cut in individual pieces for each transducer, and can cover most of the piezoelectric plate 33 back surface with the exception of an opening to allow connection 42 of individual wire 38 to electrode 39, and connection 41 to another individual wire 38 to electrode 40b. In other embodiments, air back layer 36 can be a long band that can cover groups of transducers 23 or 24 or all transducers 23 or 24 of a flexible transducer array.

For clarity, for both FIGS. 7A and 7B, air back layer 36 can be cut in individual pieces and placed on the back of each transducer, or can be a single piece that covers all transducers or groups of transducers of an array.

FIG. 7B shows a further embodiment of how the array of transducers 24 can be interconnected using flexible cable 37 with individual wires 38. Only three transducers 24 are illustrated for exemplification but it is understood that there can be several, for example sixteen buccal transducers 24 which can be connected in this manner. This transducer array configuration can also apply to lingual transducers 23. A combination of the embodiments illustrated in FIGS. 7A and 7B can be used together in ultrasonic dental attachment 3.

FIG. 7B shows a pattern of electrodes 39 and 40b seen on the back of piezoelectric plates 33. The illustrated embodiment can use a single common wire connected to electrode 40b which can be connected to the front electrode 40 (as the ground electrode) at connection point 41 of multiple transducers. Possible placement of flexible cable 37 and individual wires 38 and connections to electrodes 39 and 40b are shown. Connections 41, 42 can be made by soldering, or conductive glue or epoxy.

In FIGS. 7A and 7B, back electrodes 39 can be connected to individual wires 38 of flexible cable 37 while electrodes 40b (which can be connected to front electrode 40) can be connected to a common wire ground. This common rail wire can be connected to the ground of the external electronics controller 2 through connection cable 5. In further embodiments, individual wires 38 can be used for both electrodes (from the front and back of transducers 23, 24). For clarity, individual ground wires can also be used for each transducer in some embodiments.

In some embodiments, all buccal transducers 24 can be connected to a common ground wire where all electrodes 40b (which can be connected to front electrode 40) can be connected to a single common wire and all back electrodes 39 can be connected to a second common wire. This can allow driving of all buccal transducers 24 at the same time by using only two wires. Similar implementation can also be used for the lingual transducers 23.

Flexible cable 37 of the buccal transducers 24 and flexible cable 37 of the lingual transducers 23 can be both connected through connector 5a or 5b to cable 5 which can connect to external electronic controller 2. This connection can be located in the front buccal side of the incisors as shown in FIGS. 3A, 3B, 3C, 3D, and 3E.

Figure 8:
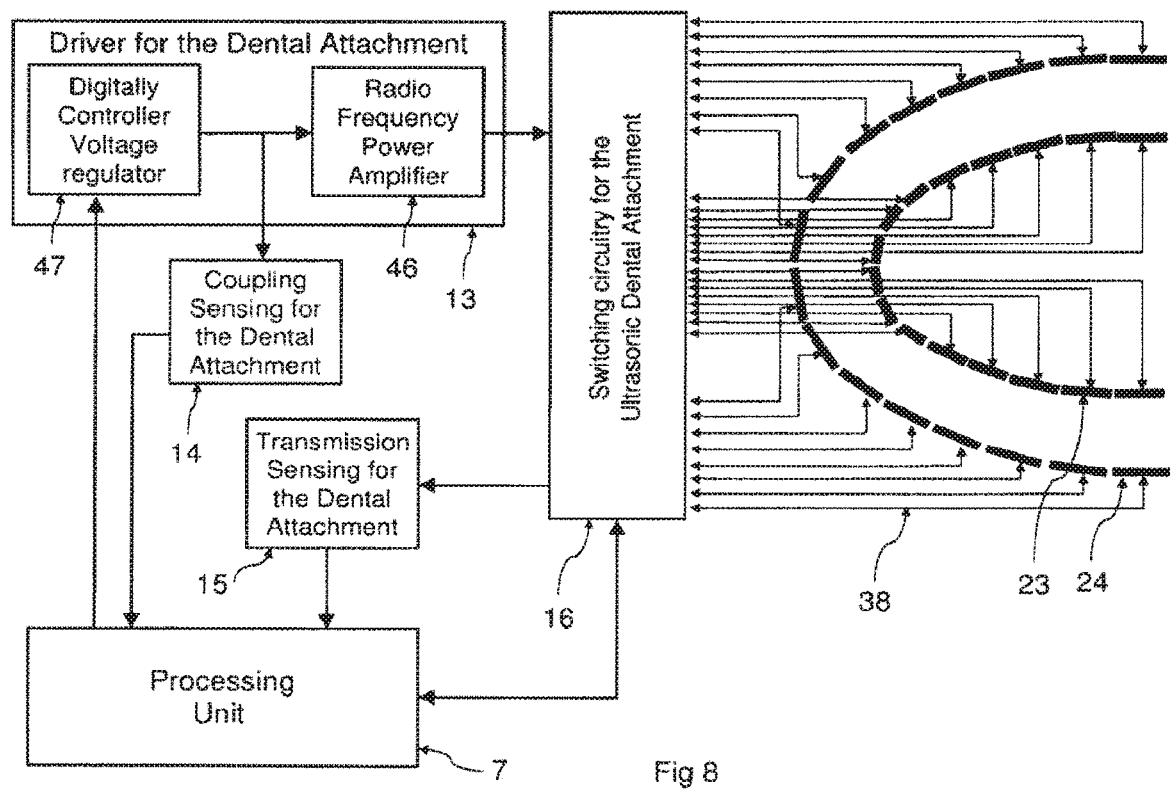
FIG. 8 is a block diagram of an embodiment of a circuitry interface with an ultrasonic dental attachment.

Referring now to FIG. 8, circuitry interface 8 from FIG. 2 is shown with ultrasonic dental attachment 3 circuitry. Driver 13 can include at least one radio frequency (RF) power amplifier 46 and at least one digitally controlled voltage regulator 47. RF power amplifier 46 can be a Class E or Class F switching amplifier. Voltage regulator 47 can be a variable voltage regulator controlled by a digital potentiometer, where the digital potentiometer can be controlled by the processing unit 7. Coupling sensing circuitry 14 can be made of a current sense circuitry that can monitor the DC current supplied by digitally controlled voltage regulator 47 to RF Power amplifier 46. The output of coupling sensing circuitry 14 can be read by an Analogue to Digital Converter (ADC) port of the processing unit 7 which can be a microcontroller.

Transmission sensing circuitry 15 can be a full-wave (or half-wave) rectifier circuitry such as bridge rectifier or diode less rectifiers, followed by an envelope detector. The output of transmission sensing circuitry 15 can be read by an Analogue to Digital Converter (ADC) port of the processing unit 7 which can be a microcontroller. Switching circuitry 16 can be located in external electronic controller 2 or in ultrasonic dental attachment 3, or a portion in controller 2 and another portion in dental attachment 3. In some embodiments, a portion of switching circuitry 16 could also be located on the cable 5 or connector 5a or 5b.

Figure 9:
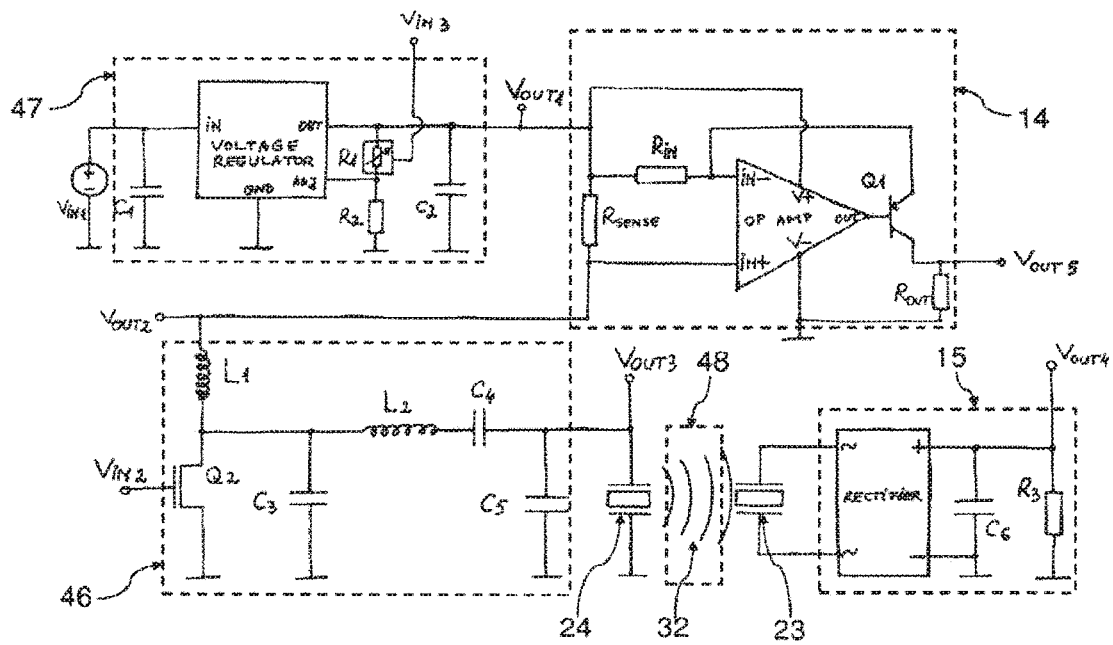
FIG. 9 is an electrical schematic of an embodiment of a circuitry interface with the dental attachment.

FIG. 9 is an electrical schematic diagram which illustrates an embodiment of the circuitry that can control transducer emitter 24 to generate ultrasonic waves 32 and can also sense the degree which transducer emitter 24 is coupled to tissue structure 48. The circuitry can also control transducer sensor 23 which can sense the transmitted waves exiting dental tissue structure 48. In order to drive multiple emitters and sensors, switching circuitry 16 can be added.

In one embodiment, Vin1 can be the power supply coming from a power source (for example, a rechargeable or non-rechargeable battery, a wall plug-in adapter) Digitally controlled voltage regulator 47 can be made of a voltage regulator with an adjustable voltage output Vout1. The voltage output Vout1 can be adjusted by a digital potentiometer R1 which can be connected to processing unit 7 such as a microcontroller digital output. Processing unit 7 can supply input signal Vin3 to digital potentiometer R1 in order to adjust the resistor value which in turn, can adjust output voltage value Vout1. In some embodiments, voltage regulator 47 can be a low-drop linear regulator LT3021 from Linear Technology.

Voltage regulator 47 can supply electrical power to an RF power amplifier 46. RF power amplifier 46 can amplify a square wave digital signal Vin2 generated by the processing unit 7. Vin2 can be a megahertz frequency signal which can be continuous or pulsed (with adjustable duty cycle), depending on the treatment settings. RF power amplifier 46 can be a Class-E power amplifier or a Class-F power amplifier. Either amplifier class can amplify the input signal Vin2 to an AC signal with the peak-to-peak voltage Vout 3 several times higher than the voltage rail Vout2. Voltage Vout2=Vout1+Voltage drop over Rsense. Rsense can have a very small value (for example, in the order of 0.001 Ohms) and therefore voltages Vout1 and Vout2 can be approximately equal.

RF power amplifier 46 can drive piezoelectric transducer 24, which emits ultrasonic waves 32 towards the dental tissue structure under ultrasonic treatment 48. The dental structure 48 can be made of layers 30, 29, 28 and 31 as illustrated in FIG. 5A.

When processing unit 7 adjusts the resistance value of the digital potentiometer R1, Vout1 and Vout2 can change. This change can modify the AC voltage (peak-to-peak voltage) Vout3 that drives the piezoelectric transducer 24 and therefore can change the ultrasonic power level of the ultrasonic waves 32 that are delivered to the tissue structure 48.

Piezoelectric transducer 23 can be placed on the opposite side of dental structure 48 and can sense the amount of ultrasonic power that exits through dental structure 48. The amount of ultrasonic power that is exiting dental structure 48 can be an indicator of the amount of ultrasonic waves that were absorbed by dental structure 48. The absorbed ultrasonic power can stimulate the repair of dental tissue. Voltage Vout4 can be related to the ultrasound power that passes from the emitter (in this example transducer 24) to the sensor (in this example transducer 23).

The electrical signal generated by piezoelectric transducer 23 can be connected to transmission sensing circuitry 15 which can condition the electrical signal received and can output voltage Vout4 that can be read by processing unit 7 (for instance an ADC port of the microcontroller). Transmission sensing circuitry 15 can be made of a rectifier such as Schottky diode bridge rectifier or non-diode rectifiers based on operational amplifiers that can also have digitally adjustable gain. For example, a suitable Schottky diode bridge rectifier can be the component MB12S from Micro Commercial Components.

The DC current supplied to RF amplifier 46 can depend on the value of the mechanical load of piezoelectric transducer 24. The electrical resistance value of the electrical impedance of piezoelectric transducer 24 can be low when it is well attached/coupled to tissue, or higher when it is not coupled to tissue. This variation of the electrical resistance value of the transducer can modify the DC current that is supplied to RF amplifier 46 and which can flow through the sensing resistor Rsense. The function of the coupling sensing circuitry 14 can be to sense the variations in the DC current supplied to RF amplifier 46. In this manner the amount or quality of the coupling of the transducer 24 to the tissue under treatment 48 can be measured by the controlling unit 7 and can alert the user. Poor coupling can indicate that ultrasonic dental attachment 3 is not placed in the mouth, is placed incorrectly in the mouth, or that ultrasonic gel needs to be added. The coupling sensing circuitry can alert the patient about the poor coupling so that corrective measures are taken which lead to improved treatment outcomes.

Coupling circuitry 14 can be a current sensing circuit. Coupling circuitry 14 can sense the DC current that flows to RF amplifier 46 by the use of a sensing resistor Rsense. The value of Rsense can be chosen to be very small (for example, on the order of milliohms), which can lead to a negligible voltage drop across the sensing resistor. Therefore, the sensing of the current can have a negligible effect on the voltage Vout2 delivered to the RF amplifier 46 and on the AC voltage Vout3 that can drive the piezoelectric transducer 24. The design of the current sensing circuit can be chosen to minimize the loss over the sensing resistor. An amplified output voltage Vout5 (which is dependent on the current through Rsense) can be provided to the ADC input of processing unit 7.

The amplification gain of the coupling sensing circuitry 14 can be configurable with two resistors Rin and Rout. Commercial current sensing circuits which include both the OP AMP and the bipolar transistor Q1 can be used, for example, the Linear Technology low-cost current sense chip LT 6106.

Processing unit 7 can receive output signal Vout4 coming from transmission sensing circuitry 15 and voltage Vout5 coming from coupling sensing circuitry 14. The ADC ports of processing unit 7 can convert these voltages into digital values. The firmware of processing unit 7 can then follow an operation algorithm and can adjust digital signal Vin3 that controls the digital potentiometer R1. Adjusting R1 can adjust in real-time the amplitude of the voltage Vout3 which can modify the amplitude of ultrasonic waves 32 and therefore modify the ultrasonic power emitted by a transducer 23 or 24. The system can adjust the amplitude of Vout3 in order to compensate for losses and absorption in the dental tissue structure 48.

Figure 10:
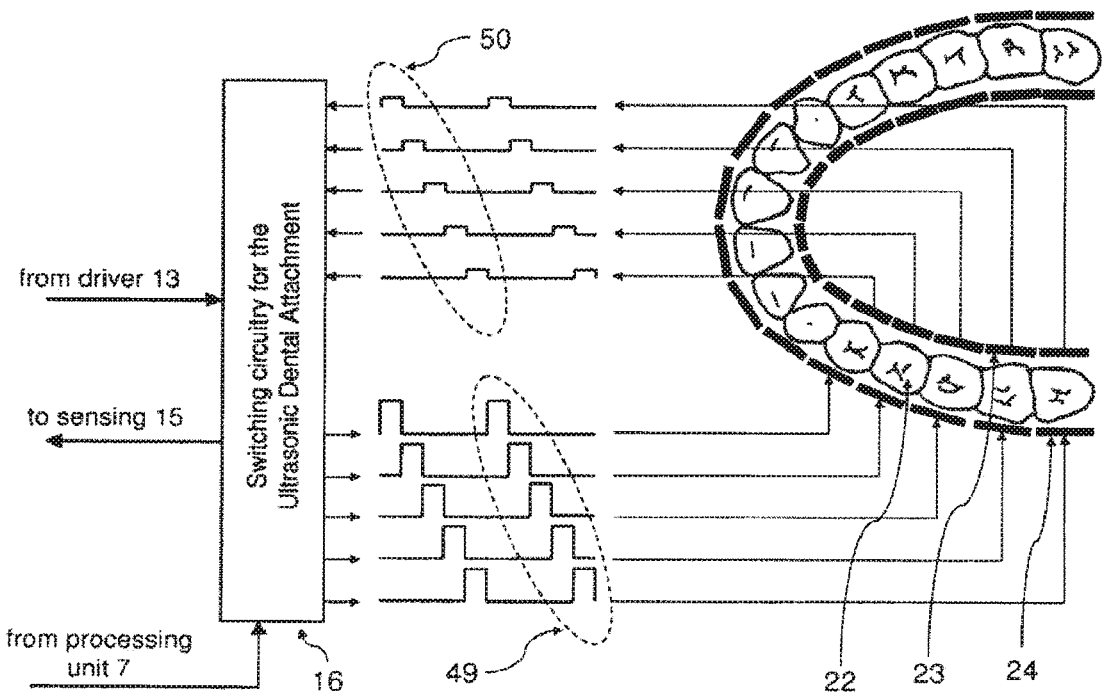
FIG. 10 is a block diagram of an embodiment of a circuit to drive multiple ultrasound transducers sequentially.

FIG. 10 shows a block diagram of one embodiment of a circuit and an algorithm which can be used to drive multiple transducers sequentially in ultrasonic dental system 1. In one embodiment, electrical signals 49 can drive transducers 24 when working in ultrasound emitting mode and electrical signals 50 can be sensed by transducers 23 when working in ultrasound sensing mode. While FIG. 10 demonstrates that five pairs of sensor/emitters are being driven, this example can also extend to the remaining pairs of sensor/emitters.

In the illustrated embodiment, the electrical signal from driver 13 can be a continuous 1.5 MHz signal which is switched to five channels 49 by switching circuitry 16. Each individual signal 49 can be a 200 microseconds burst of an oscillating 1.5 MHz signal, followed by 800 microseconds when the 1.5 MHz signal is OFF. The cycle can repeat every 1000 microseconds with 200 microseconds of the 1.5 MHz signal ON and 800 microseconds OFF. The period when the 1.5 MHz signal is ON does not overlap between the five signals. Therefore, in a period of 1000 microseconds (or 1 millisecond) only one transducer will emit at a time. This type of staggering can be used to avoid interference between the five transducers that emit, although it would be understood that other values could be used to accomplish the same goal.

Transducer 24 (in the emitting mode) can be driven by a signal of 1.5 MHz that can be modulated at a 1 KHz with 20% duty cycle. These parameters are provided for examples only. Different MHz signals can be used other than 1.5 MHz, different modulation signals other than 1 KHz can be used, and duty cycles different than 20% can also be used.

Each individual signal 50 coming from transducer 23 (in a sensing mode) can be a delayed replica of emitted signal 49, but with the amplitude of the oscillation decreased due to absorption of the ultrasound in the dental tissue. Only the amplitude will be reduced. The carrier frequency (for example here 1.5 MHz), the modulation frequency (for example here 1 KHz) and the duty cycle (for example here 20%) can remain unchanged.

In this example five transducers 24 can emit ultrasound sequentially (one after another, not in the same time) and five transducers 23 can sense the ultrasound. This can be done using a single driving circuitry 13, a single sensing circuitry 14 and a single sensing circuitry 15. By the use of switching circuitry 16, transducers 24 can be switched to sensing mode and the transducers 23 can be switched to emitting mode. In this way the ultrasonic treatment can be delivered from either side of the tooth. Switching circuitry 16 can be made, for example, of one or more multiplexer/demultiplexer circuits such as the analogue sixteen channel multiplexer/demultiplexer HCF4067 from STMicroelectronics.

In one example, a single transducer 24 can emit ultrasound and a single transducer 23 (located on the other side of tooth 22) can sense ultrasound. In addition, by using the switching circuitry 16, in some embodiments three neighboring transducers 23 (centered on the other side of teeth 22 the emitter transducer 24) can be connected together to sense at the same time. In this manner three neighboring transducers 23 that are sensing can form a larger sensing area and can receive more of the diverging and scattered ultrasound waves coming from an emitting transducer 24. In this example, the 1.5 MHz signal from the processing unit 7 (microcontroller) can be switched so that one transducer 24 can emit from the buccal side, and three transducers 23 can sense on the lingual side. This can increase the amplitude of the electrical signal of the sensor transducers and improve the sensing capability of the system. Alternatively, by using switching circuitry 16, one transducer 23 (from the lingual side) can emit ultrasound and three transducers 24 (from the buccal side) can sense ultrasound.

In a further example, teeth 22 with similar properties (thickness, length etc) can be grouped together. For example, the four incisors=group one, the left canine and the two left premolars=group two, the right canine and the two right premolars=group three, the three left molars=group four, and the three right molars=group five. Each group can be driven at once, and the circuitry shown in FIG. 10 can therefore drive all the five groups sequentially.

For the cases where each individual tooth 22 has to be treated separately from each other, then ultrasonic dental system 1 can be setup in the following two ways: switching circuitry 16 can drive treatment of five teeth sequentially for the duration of the treatment (for example 20 minutes) and then can pass to the next five teeth for another 20 minutes of treatment, or alternatively interface circuitry 8 can have multiple blocks that each can drive treatment of five teeth sequentially.

Ultrasonic dental system 1 can have the ability to sense, in real-time, the intensity of the ultrasound waves emitted to the tissue and can adjust this intensity to the optimum desired range. This adjustment can be performed in real-time, for each individual tooth or for all teeth at the same time, as desired.

The effects of ultrasound on dental tissue and bone tissue can be dependent on the intensity of the ultrasound used in treatment. Levels of intensity lower then an optimum level can result in poor tissue stimulation, while levels of intensity higher then an optimum level can result in tissue damage. When an ultrasonic wave propagates through dental tissue it can be absorbed by the tissue and the intended ultrasound intensity initially sent by an emitter can be reduced. As such, tissue further away from an emitter can be less stimulated. Ultrasonic dental system 1 can provide uniform ultrasound treatment (uniform ultrasonic intensity) to a treatment area by targeting ultrasound waves to a treatment area from opposite sides of the treatment area at different times. By emitting from the different directions at different times, wave interference can be reduced or avoided. For example, when ultrasound waves are emitted from the buccal side of a treatment area for 200 microseconds followed by no emission for 800 microseconds, and ultrasound is being emitted from the lingual side of the treatment area for a different 200 microseconds and followed by no emission for 800 microseconds, then within a total period of 1000 microseconds, a treatment area can receive 200 microseconds of treatment from the lingual side and another 200 microseconds of treatment from the buccal side without interference. In order to avoid wave interference, there can be no time of overlap between the two periods of ultrasound emission. By treating both sides of a treatment area within a 1000 microsecond modulation period, a standard daily treatment time (for example, twenty minutes) does not need to be increased.

Figure 11:
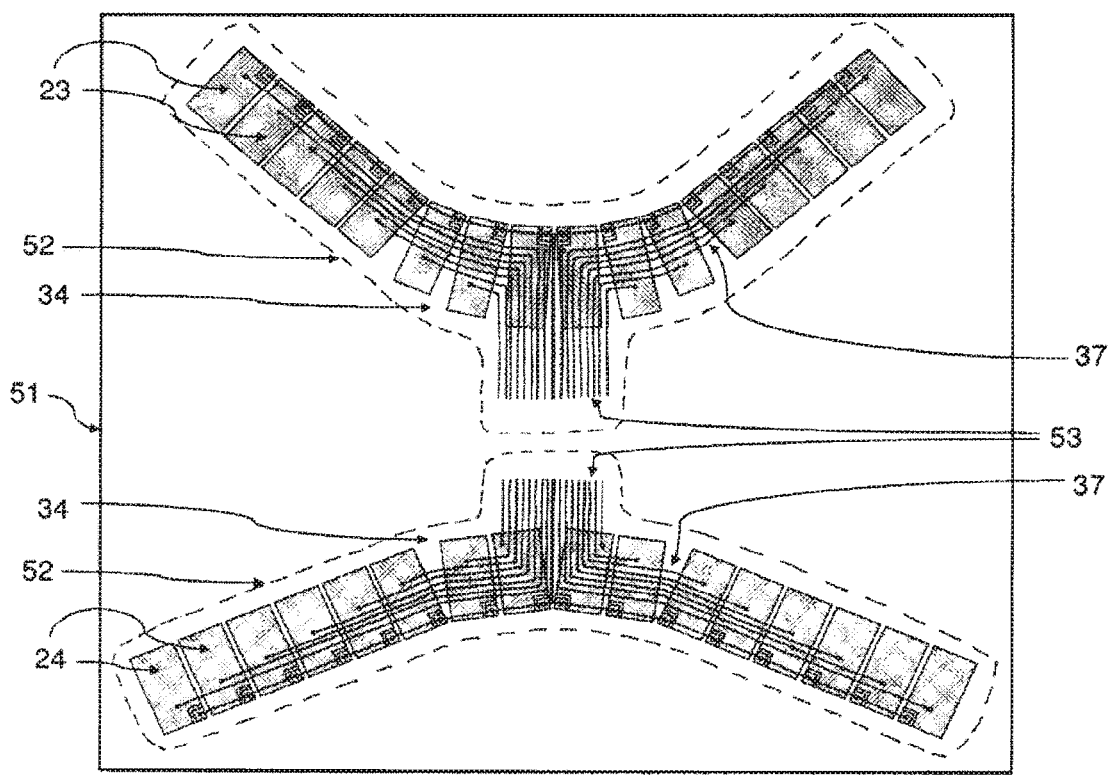
FIG. 11A is a schematic diagram outlining a manufacturing method of an embodiment of the ultrasonic dental system.
FIG. 11B is a close up view of FIG. 11A, and outlines an embodiment of connecting pads and an embodiment of a connector.

Referring now to FIG. 11A, one process for manufacturing ultrasonic dental attachment 3 is shown, however other processes can be employed to manufacture dental attachment 3. Combinations of the processes are also contemplated.

A flat sheet 51 of flexible material is provided. Flat sheet 51 can be made of polypropylene, copolyester or EVA. The thickness of flat sheet 51 can be a quarter of an ultrasound wavelength. For example, for EVA material the thickness of flat sheet 51 can be on the order of 0.3 mm for ultrasonic waves at the frequency of 1.5 MHz. The exact value of the thickness of flat sheet 51 can depend on the specific properties of the material.

An outline 52 of flat sheet 51 around the array of ultrasound transducers 23 and 24 can delimit the area of the acoustic impedance matching layer 34. The end connecting pads 53 of flexible cable 37 for the buccal and lingual side are shown. In some embodiments, flexible cable 37 for both lingual and buccal arrays can be separate pieces. In some embodiments, flexible cable 37 for both of the lingual and buccal portions can be continuous (for example, one piece).

Figure 11B:
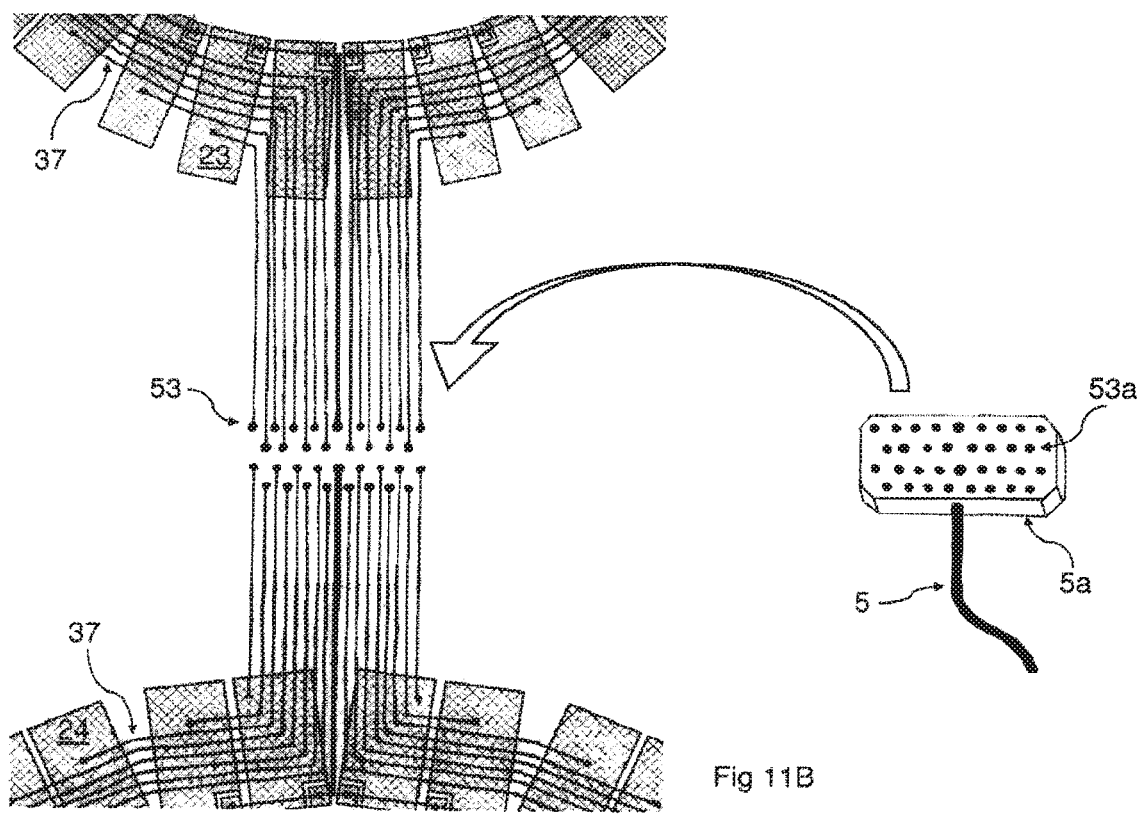

Referring now to FIG. 11B, a close up version of FIG. 11A and connections means are shown. Connecting pads 53 of flexible cable 37 of the lingual and buccal transducers, can form an array of pads as part of flexible cable 37. This array of pads 53 can connect to a second array of pads 53a. The array of pads 53a can form the embedded connector 5a, which can connect to cable 5 which can further connect the overall ultrasonic dental attachment 3 to the external electronics controller 2. The array of pads 53 (of flex cable 37) can be attached to array of pads 53a (of embedded connector 5a) in a temporary or permanent fashion, by use of conductive epoxy/glue or soldering, or by any suitable mechanical attachment for example.

A first method of manufacturing can be outlined by the following steps:

Step 1: Attachment (by glue or by heat) of the array of buccal transducers 24 and lingual transducers 23 on flat sheet 51 on a flat surface in the pattern shown in FIG. 10. Front electrodes 40 of transducers 23, 24 can be facing down to sheet 51.

Step 2: Interconnection of the transducers that form the buccal and lingual array of transducers. If the transducer embodiment illustrated in FIGS. 6A and 7A is used, connect flexible cable 37 to back electrodes 39 (connections 41 and 42 for each transducer 23 or 24) as illustrated in FIG. 7A. Next, air back layer 36 can be attached on top of flexible cable 37 as illustrated in FIG. 6A. Alternatively, the transducer embodiment illustrated in FIGS. 6B and 7B can also be used. Steps 1 and 2 can be interchanged so that the array of transducers 23 and 24 can also be attached to flat sheet 51 after the interconnections are realized.

Step 3: Cutting flat sheet 51 around the transducer arrays keeping a border of few millimeters as illustrated by dashed line 52. The area encompassed by dashed line 52 represents acoustic impedance matching layer 34 that can come in contact with the gums.

Step 4: Positioning the two arrays of transducers (attached to the cut up of sheet 51) on dental cast 21. Layer 34 of the transducer arrays can contact and cover the tooth roots, as illustrated in FIG. 3A.

Step 5: Forming a second flat sheet 51 over dental cast 21 and the transducer arrays. The second flat sheet 51 can be applied by using vacuum or pressure thermoforming, by coating with a liquid form of the flexible material found in sheet 51 or by deposition (sputtering, spraying).

Step 6: Connection of the connecting pads 53 over the incisors to external cable 5. The connection can be sealed with epoxy or another local thermoforming or coating step.

Step 7: The edges of the second flat sheet 51 that was applied over the dental cast and transducers can be trimmed around the bottom side of the transducer array. A few millimeters of overlapping between the two flexible materials can be kept in order to secure sealing of the internal components of ultrasonic dental attachment 3.

This manufacturing method can ensure that layer 34 will have a well controlled thickness of a quarter wavelengths, and this thickness will not be altered during the manufacturing process.

A further method of manufacturing can be outlined by the following steps:

Step 1: Forming a layer of flat sheet 51 over dental cast 21 by using thermoforming or by coating. The thickness of flat sheet 51 in the area next to the tooth roots can be a quarter of an ultrasound wavelength thick. If thermoforming is used for this step, the thickness of layer 34 can be controlled by controlling the temperature of the flexible sheet during thermoforming.

Step 2: Interconnecting the transducers that form the buccal and lingual array of transducers. If the transducer embodiment illustrated in FIGS. 6A and 7A is used, connect flexible cable 37 to back electrodes 39 (connections 41 and 42 for each transducer 23 or 24) as illustrated in FIG. 7A. Next, air back layer 36 can be attached on top of flexible cable 37 as illustrated in FIG. 6A. Alternatively, the transducer embodiment illustrated in FIGS. 6B and 7B can be used.

Step 3: Attaching (using glue or thermal process) the two arrays of transducers (buccal and lingual) on flat sheet 51 which can cover dental cast 21. Transducers can be positioned at the location of the tooth roots.

Step 4: A second flat sheet 51 can be placed over the transducer arrays which are placed on the first flat sheet 51 that was placed over the dental cast. The second flat sheet can be applied by using vacuum or pressure thermoforming, by coating with a liquid form of the flexible material found in sheet 51 or by deposition (sputtering, spraying).

Step 5: Connection of the connecting pads 53 over the incisors to external cable 5. The connection can be sealed with epoxy or another local thermoforming or coating step.

Step 6: The edges of flat sheets 51 can be trimmed around the bottom side of the transducer array. A few millimeters of overlapping between the two flexible materials can be kept in order to secure sealing of the internal components of ultrasonic dental attachment 3.

In some embodiments of the above manufacturing method, Step 1 can be skipped, and the method commences at Step 2. Then the lingual and buccal arrays of transducers can be placed on metal stands and thermoformed from the side, so that one thermoforming process can completely seal around the transducer array. The stands can be removed and the orifices sealed with heat or glue. The thickness of the encapsulation layer can be controlled by controlling the temperature during thermoforming. At Step 3 the lingual and buccal arrays can be placed on a bare dental cast. Follow steps 4, 5 and 6 as above.

A further method of manufacturing can be outlined by the following steps:

Step 1: Interconnecting the transducers that form the buccal and lingual array of transducers. If the transducer embodiment illustrated in FIGS. 6A and 7A is used, flexible cable 37 can be connected to back electrodes 39 (connections 41 and 42 for each transducer 23 or 24) as illustrated in FIG. 7A. Next, air back layer 36 can be attached on top of flexible cable 37 as illustrated in FIG. 6A. Alternatively, the transducer embodiment illustrated in FIGS. 6B and 7B can be used.

Step 2: Placing the two arrays of transducers in a negative injection mold shell with the shape of dental cast 21. The position of the transducer arrays inside the injection mold shell can be predetermined such as to form a layer of quarter of an ultrasound wavelength thickness between the transducer surface and the gums 30,31.

Step 3: Connect connecting pads 53 to cable 5 at a location inside or outside the shell.

Step 4: Fill (injection mold) the cast with melded or liquid form of the flat sheet 51 material (for example, EVA, polypropylene, or copolyester).

Step 5: Cure and trim the interior part of the injection mold.

Dental cast 21 can be custom designed for each patient or can be a generic shape. If a generic dental cast is used, then the patient can customize the ultrasonic dental attachment 3 to their own teeth. The material of flat sheet 51 can be reshaped when heated (for instance in boiling water) and can be used to perform this function by a patient at home. In some embodiments, a bite pad 25a can be used to accommodate the shape of the user's teeth.

Figure 12A:
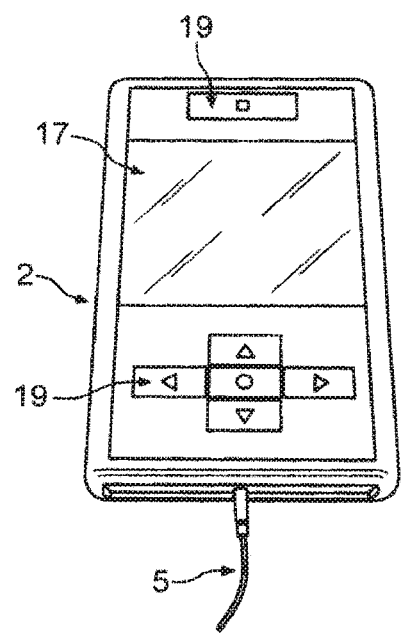
FIG. 12A is a front view of an embodiment of an external electronics controller.
Figure 12B:
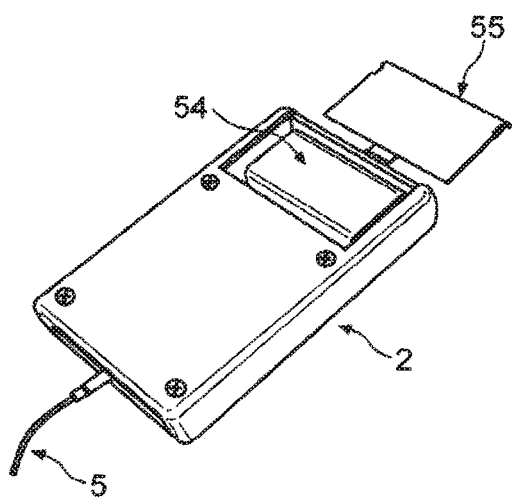
FIG. 12B is a rear view of an embodiment of an external electronics controller.

Referring now to FIGS. 12A and 12B, a front and rear view of an embodiment of external electronics controller 2 are shown. The front panel of external electronics controller 2 can have user interface elements such as display 17 (LCD or touch screen) and push buttons 19 which can allow a user (patient or dentist) to operate and interact with ultrasonic dental system 1. External electronics controller 2 may also include a speaker (not shown).

In some embodiments, a user can turn on/off the device using the button 19, can receive information on the treatment status from display 17, and can be alerted by display 17 and speaker if there is a malfunction or a low power level. External electronics controller 2 and its interface can allow the setting of the ultrasonic dental system 1 prior to ultrasonic treatment. A user can turn on only the emitter-sensor pairs for the teeth that have to be treated and not treat healthy teeth. In some embodiments external electronics controller 2 can record treatment data which can be later verified by the user in order to ensure treatment compliance and improve treatment outcomes.

External electronics controller 2 can be battery powered or powered from the wall using a plug-in adapter. The rear panel of external electronics controller 2 can provide access to battery 54. Battery compartment can be covered by cover 55. The rear panel of external electronics controller 2 can also provide access to a connection port such as USB (for connection to a computer) or connector for power supply or battery charging.

In some embodiments of ultrasonic dental system 1, the electronics from the external electronics controller 2 and battery can be fit inside the ultrasonic dental attachment 3. In this embodiment, the user interface (display 17, push buttons 19) can be kept outside the mouth and can communicate through a cable or wirelessly to the intra-oral electronics. The intra-oral electronics can be a rigid or flexible printed circuit board (FPC) that can be placed on top of the teeth or on the buccal or lingual side of the teeth crowns and roots.

The thicknesses of the dental structures (gum, alveolar bone, periodontal ligaments) can be at the order of the wavelength of the ultrasonic waves of around 1 mm in aqueous media. As such, the intensity of ultrasound waves can be severely affected during propagation through these multilayer structures and can also be reflected when exiting into air or a sensor. The use of anti-reflection type coatings on ultrasonic dental attachment 3 can allow for desired coupling of the waves from emitter and sensor and subsequently can allow for a more accurate power reading at the sensor. Use of an anti-reflection coating can increase the energy that contacts and enters the sensor and is absorbed and converted into electrical signal. Use of an anti-reflection coating can also reduce or eliminate the reflection of waves back onto the tooth. Our manufacturing methods solve this problem.

The surface of transducers 23, 24 and the interior of ultrasonic dental attachment 3 can be coated with a compound that can change color when in contact with water (for example, a humidity/moisture indicator material similar to the humidity indicator cards or stickers available on the market). For example, if a crack forms in ultrasonic dental attachment 3 and water or saliva leak into it, then the user can observe a change in color and discontinue using ultrasonic dental attachment 3.

In operation, ultrasonic dental system 1 can have ultrasonic dental attachment 3 connected to external electronic controller 2. External electronic controller 2 can instruct a user on a treatment procedure and treatment status. Ultrasonic dental attachment 3 can be placed inside the patient's mouth during an ultrasonic treatment for a duration, for example of 20 minutes per day. In some embodiments, external electronic controller 2 can generate, monitor and adjust in real-time a dosage of ultrasound delivered to the desired area, can display the treatment status and can record the treatment parameters. In some embodiments, the transducers can be cooperative and can act in cooperation when emitting and sensing ultrasound. When bitten, ultrasonic dental attachment 3 can closely follow the shape of a dental arch allowing for a patient to repeatedly place ultrasonic dental attachment 3 in the correct position. This consistent positioning can ensure the appropriate delivery of ultrasound to the desired area. A dental professional can diagnose a clinical condition of a patient, and can indicate which teeth could benefit from ultrasound treatment. By accessing a menu section of the external electronic controller 2, the user can set ON the emitter-sensor pairs for the teeth of interest. The user can follow instructions displayed on external electronic controller 2. Ultrasonic dental system 1 can treat different teeth or implants requiring different dental treatments at the same time, on the same patient. Interchangeable emitters and sensors can give an improved uniformity of treatment and can improve patient outcome. Ultrasonic waves can be alternatively emitted from either side of a tooth. In some embodiments, ultrasonic waves are not emitted from both sides of a tooth at the same time as this can lead to wave interference. For example, a first treatment can have waves emitted from the lingual transducers and sensed by the buccal transducers, while in a subsequent treatment the waves can be emitted by the buccal transducers and sensed by the lingual transducers. By alternating the side being treated, ultrasonic dental system 1 can ensure that the ultrasound treatment is uniform on both sides which can lead to an improved patient outcome.

In some embodiments, ultrasonic dental system 1 can provide a method to accelerate the orthodontic tooth movement without applying any additional force (cyclical and/or continuous) to a tooth crown. The application of ultrasound dental treatment as described herein can result in accelerated orthodontic tooth movement while not affecting the amount and direction of the forces applied by the orthodontic appliance to the tooth crowns. The application of ultrasound can affect the speed of tooth movement by accelerating the processes involved in the alveolar bone remodeling around the tooth roots. The use of ultrasonic dental system 1 can eliminate the need for temporary anchorage devices for orthodontic tooth movement and space closure as it selectively accelerate only the teeth of interest and not the anchorage teeth. The use of ultrasonic dental system 1 can increase the movement ratio between target tooth and anchorage tooth.

In some embodiments, ultrasonic dental system 1 can include self-calibration capabilities and self-adjusting coupling sensing. Ultrasonic dental system 1 can measure the electrical impedance of the ultrasonic dental device when in the air (which can be the worst coupling scenario), and the electrical impedance when in water (which can be the best coupling scenario). When dental attachment 3 is placed in the mouth with ultrasonic gel, the electrical impedance can be similar to the scenario in the water. Processing unit 7 can then activate the ultrasonic treatment. If the dental attachment 3 is not placed in the mouth or gel was not used correctly, then the electrical impedance reading can be different than the water reading, and closer to the in-air reading. In some embodiments, processing unit 7 will not activate the ultrasonic treatment and can alert the patient to use gel or place attachment correctly in the mouth. As such, the deciding if dental attachment 3 is correctly applied can be taken based on electrical impedance measurements in the air and in the water. The two electrical impedance reference points can vary with attachment 3 wearing or becoming physically damaged. To detect these longer term changes, the microcontroller records and stores electrical impedance measurements in the air and in the water periodically. If these values vary from the previously stored values, it can indicate that the ultrasonic attachment 3 properties have changed. If the difference between values is not significant then processing unit 7 can adjust the driving voltage of the transducers based on an internal formula/model in order to compensate and correct for the change in impendence and keep can the ultrasonic intensity in the desired range, for example 30 mW/cm2. In some embodiments, if the difference is significantly greater than the pre-determined threshold, processing unit 7 will not activate the ultrasonic treatment and can alert the user to service the device.

Although a few embodiments have been shown and described, it will be appreciated by those skilled in the art that various changes and modifications might be made without departing from the spirit or scope of the invention. Unless defined otherwise, all technical and scientific terms used herein have the same meaning as commonly understood to one of ordinary skill and the art to which this invention belongs. In addition, the terms and expressions used in the preceding specification have been used herein as terms of description and not of limitation, and there is no intention in the use of such terms and expressions of excluding equivalents of the features shown and described or portions thereof, it being recognized that the scope of the invention is defined and limited only by the claims that follow.

I claim:

1. A system for use in emitting ultrasound to a dental area, the system comprising:
    an intra-oral dental attachment for providing ultrasound emissions to the dental area; the dental attachment comprising at least one flexible array of cooperative ultrasound transducers; and
    controlling means for controlling the ultrasound emissions, the controlling means being in communication with the dental attachment;
    wherein the at least one flexible array of cooperative ultrasound transducers comprises:
        at least one buccal side transducer and at least one lingual side transducer, which are each independently and selectively controllable by the controlling means to: emit ultrasound in an ultrasound emitting mode;
    and to sense at least one stimulus and provide feedback in an ultrasound sensing mode; and
        wherein the controlling means independently and selectively controls the at least one buccal side transducer and at least one lingual side transducer based, at least in part, on the feedback, and
        wherein the controlling means comprises switching circuitry coupled to the at least one buccal side transducer and at least one lingual side transducer, the switching circuitry comprising one or more multiplexer/demultiplexer circuits selectively switching each of the at least one buccal side transducer and the at least one lingual side transducer between the ultrasound emitting mode and the ultrasound sensing mode.

2. The system of claim 1 further comprising an acoustic impedance matching layer disposed between the at least one flexible array and the dental area.

3. The system of claim 1 further comprising an external base station in communication with the controlling means.

4. The system of claim 1 wherein the sensed stimulus is a value of electrical impedance of the ultrasound transducers.

5. The system of claim 1 wherein the sensed stimulus is ultrasound.

6. The system of claim 1 wherein the dental attachment further comprises a housing for containing the at least one flexible array and an acoustic impedance matching layer, where the housing positions the at least one flexible array of ultrasound transducers in a manner to provide ultrasound treatment to the dental area.

7. The system of claim 1 wherein the controlling means comprises a processing unit, a power supply, and at least one voltage regulator.

8. The system of claim 1 wherein the controlling means comprises intraoral components and extraoral components.

9. The system of claim 8 wherein the intraoral components comprise electronics for the controlling means and the extraoral components comprise a user interface in communication with the electronics.

* * * * *